United States Patent [19]

Kleinert

[11] Patent Number: 5,182,266
[45] Date of Patent: Jan. 26, 1993

[54] METHOD FOR TREATING RENAL DISEASE

[75] Inventor: Hollis D. Kleinert, Buffalo Grove, Ill.

[73] Assignee: Abbott Laboratories, Abbott Park, Ill.

[21] Appl. No.: 836,560

[22] Filed: Feb. 14, 1992

Related U.S. Application Data

[63] Continuation of Ser. No. 632,595, Jan. 4, 1991, which is a continuation-in-part of Ser. No. 472,937, Jan. 31, 1990, abandoned.

[51] Int. Cl.$^5$ ............................................. A61K 37/00
[52] U.S. Cl. ...................................................... 514/18
[58] Field of Search ................................ 514/280, 18

[56] References Cited

U.S. PATENT DOCUMENTS

| | | | |
|---|---|---|---|
| 4,081,553 | 3/1978 | Robert | 514/530 |
| 4,466,973 | 8/1984 | Renule | 514/330 |
| 4,721,776 | 2/1988 | Raddatz et al. | 514/323 |
| 4,729,999 | 3/1988 | Young | 514/227 |
| 4,837,204 | 6/1989 | Rosenberg et al. | 514/18 |
| 4,845,079 | 7/1989 | Luly et al. | 514/18 |
| 4,906,613 | 3/1990 | Watkins | 514/16 |
| 4,952,581 | 8/1990 | Bito | 514/236 |
| 4,981,871 | 1/1991 | Abelson | 514/523 |
| 5,006,560 | 4/1991 | Kreutner et al. | 514/114 |

FOREIGN PATENT DOCUMENTS

| | | |
|---|---|---|
| 0189203 | 7/1986 | European Pat. Off. |
| 0264106 | 4/1988 | European Pat. Off. |
| 0307837 | 3/1989 | European Pat. Off. |
| 0341602 | 11/1989 | European Pat. Off. |
| WO88/05050 | 7/1988 | PCT Int'l Appl. |
| WO90/03971 | 4/1990 | PCT Int'l Appl. |

OTHER PUBLICATIONS

Chem. Abst.-111-134757w (1989).
Chem. Abst. 112-99255c (1990).
Neisius, et al., Am. J. Physiol. 251 H897-H902 (1986).
Siragy, et al., Am. J. Phys. 255 F749-F754 (1988).
Verburg, et al., Kidney International 35 304 (1989).
Mutschler, "Arzneimittelwirkungen":, Lehrbuch der Phamakologie und Toxikologie ed. 5 pp. 334–335 (1986).

*Primary Examiner*—S. J. Friedman
*Attorney, Agent, or Firm*—Steven R. Crowley

[57] ABSTRACT

The present invention relates to the use of renin inhibitors and to renin inhibitor compositions for prevention, treatment, inhibition or reversal of renal dysfunction or disease, especially renal failure.

4 Claims, No Drawings

METHOD FOR TREATING RENAL DISEASE

This is a continuation of U.S. patent application Ser. No. 07/632,595, filed Jan. 4, 1991 which is a continuation-in-part of U.S. patent application Ser. No. 472,937, Filed Jan. 31, 1990 now abandon.

TECHNICAL FIELD

The present invention relates to the use of renin inhibitors and to renin inhibitor compositions for prevention, treatment, inhibition or reversal of renal dysfunction or disease, especially renal failure.

BACKGROUND ART

Renal dysfunction or disease includes acute renal failure and chronic renal failure. In general, renal diseases are characterized by one or more of the following: reduced renal blood flow, reduced glomerular filtration rate, proteinuria, hematuria and alterations in water and sodium excretion.

Acute renal failure is a condition characterized by an abrupt and sustained reduction in glomerular filtration rate (GFR) occuring within a period of hours in response to an acute ischemic or nephrotoxic insult. Acute renal failure is not immediately reversible when the initial disturbance has been eliminated. Immediate improvment in GFR and increasing fluid flow through the nephron appears to be of critical importance in the prognosis of acute renal failure.

Chronic renal failure is characterized by (1) a reduction in GFR that has been evident for 3 to 6 months, (2) a continual decline in GFR over a period of years and (3) symptoms of uremia. The term renal insufficiency is often used to characterize a condition in which a mild reduction in GFR has occurred, but no uremic symptoms have appeared. Chronic renal failure denotes irreversible nephron loss, wheras acute renal failure reflects a reduction in single nephron GFR due to potentially reversible nephron injury.

Proteinuria (elevated urinary excretion of plasma proteins) can be present during acute and chronic renal failure and has been shown to be an accurate index of the extent of glomerular damage (Dennis, et al., in *The Kidney: Physiology* and *Pathophysiology*, edited by D. W. Seldin and G. Giebisch, Vol. 2, pp. 1805–1818, Raven Press, N.Y., 1985). Agents that reduce proteinuria have been shown to have beneficial effects on glomerular injury (Anderson, et al., J. Clin. Invest. 76 612 (1985)).

It is believed that angiotensin II plays a role in renal failure. Angiotensin II (AII) is a peptide hormone that is produced in the kidney in a two step process, the first step of which is the cleavage of angiotensinogen by the enzyme renin. Renin is stored primarily in the juxtaglomerular cells of the kidney.

Angiotensin II has profound effects on the kidney, including direct vasoconstriction of the renal vascular bed thereby altering renal blood flow, stimulation of sodium reabsorption, modification of glomerular feedback, alteration of GFR through changes in either the hydraulic pressure or by reducing the filtration surface area secondary to mesangial cell contraction, and increasing distal nephron sodium reabsorption indirectly through stimulation of aldosterone secretion. In addition, AII increases the passage of circulation macromolecules into the glomerular mesangium and decreases their egress. All of these effects of angiotensin II have a negative impact on renal disease. Therefore, an agent that prevents or inhibits the formation of angiotensin II, such as a renin inhibitor, can have a beneficial effect on renal disease. Renin inhibitors have been disclosed as agents for treating systemic hypertension and there are no known side effects which result when renin is inhibited from acting on its substrate.

DISCLOSURE OF THE INVENTION

It has now been discovered that renin inhibitors are useful for the prevention, treatment, inhibition or reversal of renal dysfunction or renal disease and in particular renal failure.

Examples of renin inhibitors and the methods for preparing the renin inhibitors include, but are not limited to, those disclosed in the following references, which are hereby incorporated by reference.

References Disclosing Renin Inhibiting Compounds

1. Luly, et al., U.S. Pat. No. 4,652,551, issued Mar. 24, 1987.
2. Luly, et al., U.S. Pat. No. 4,645,759, issued Feb. 24, 1987.
3. Luly, et al., U.S. Pat. No. 4,680,284, issued Jul. 14, 1987.
4. Luly, et al., U.S. Pat. No. 4,725,583, issued Feb. 16, 1988.
5. Luly, et al., U.S. Pat. No. 4,725,584, issued Feb. 16, 1988.
6. Riniker, et al., U.S. Pat. No. 4,595,677 issued Jun. 17, 1986.
7. Fuhrer, et al., U.S. Pat. No. 4,613,676, issued Sep. 23, 1986.
8. Buhlmayer, et al., U.S. Pat. No. 4,727,060, issued Feb. 23, 1988.
9. Buhlmayer, et al., U.S. Pat. No. 4,758,584, issued Jul. 19, 1988.
10. Iizuka, et al., U.S. Pat. No. 4,656,269, issued Apr. 7, 1987.
11. Iizuka, et al., U.S. Pat. No. 4,711,958, issued Dec. 8, 1987.
12. Veber, et al., U.S. Pat. No. 4,384,994, issued May 24, 1983.
13. Boger, et al., U.S. Pat. No. 4,470,971, issued Sep. 11, 1984.
14. Boger, et al., U.S. Pat. No. 4,477,440, issued Oct. 16, 1984.
15. Boger, et al., U.S. Pat. No. 4,477,441, issued Oct. 16, 1984.
16. Veber, et al., U.S. Pat. No. 4,479,941, issued Oct. 30, 1984.
17. Boger, et al., U.S. Pat. No. 4,485,099, issued Nov. 27, 1984.
18. Boger, et al., U.S. Pat. No. 4,668,663, issued May 26, 1987.
19. Boger, et al., U.S. Pat. No. 4,665,052, issued May 12, 1987.
20. Bock, et al., U.S. Pat. No. 4,636,491, issued Nov. 3, 1987.
21. Boger, et al., U.S. Pat. No. 4,661,473, issued Apr. 28, 1987.
22. Bock, et al., U.S. Pat. No. 4,663,310, issued May 5, 1987.
23. Evans, et al., U.S. Pat. No. 4,609,641, issued Sep. 2, 1986.
24. Evans, et al., U.S. Pat. No. 4,665,055, issued May 12, 1987.
25. Boger, et al., U.S. Pat. No. 4,668,770, issued May 26, 1987.

26. Boger, U.S. Pat. No. 4,743,584, issued May 10, 1988.
27. Raddatz, et al., U.S. Pat. No. 4,666,888, issued May 19, 1987.
28. Holzemann, et al., U.S. Pat. No. 4,709,010, issued Nov. 24, 1987.
29. Raddatz, et al., U.S. Pat. No. 4,721,776, issued Jan. 26, 1988.
30. Raddatz, et al., U.S. Pat. No. 4,755,592, issued Jul. 5, 1988.
31. Hoover, U.S. Pat. No. 4,599,198, issued Jul. 8, 1986.
32. Bindra, et al., U.S. Pat. No. 4,729,985, issued Mar. 8, 1988.
33. Hoover, U.S. Pat. No. 4,668,769, issued May 26, 1987.
34. Bindra, et al., U.S. Pat. No. 4,749,687, issued Jun. 7, 1988.
35. Matsueda, et al., U.S. Pat. No. 4,548,926, issued Oct. 22, 1985.
36. Matsueda, et al., U.S. Pat. No. 4,698,329, issued Oct. 6, 1987.
37. Cazaubon, et al., U.S. Pat. No. 4,481,192, issued Nov. 6, 1984.
38. Wagnon, et al., U.S. Pat. No. 4,725,580, issued Feb. 16, 1988.
39. Hansen, et al., U.S. Pat. No. 4,510,085, issued Apr. 9, 1985.
40. Hansen, et al., U.S. Pat. No. 4,514,332, issued Apr. 30, 1985.
41. Baran, et al., U.S. Pat. No. 4,657,931, issued Apr. 14, 1987.
42. Hansen, et al., U.S. Pat. No. 4,722,922, issued Feb. 2, 1988.
43. Ryono, et al., U.S. Pat. No. 4,616,088, issued Oct. 7, 1986.
44. Ryono, et al., U.S. Pat. No. 4,665,193, issued May 12, 1987.
45. Ryono, et al., U.S. Pat. No. 4,629,724, issued Dec. 16, 1986.
46. Natarajan, et al., U.S. Pat. No. 4,757,050, issued Jul. 12, 1988.
47. Gordon, U.S. Pat. No. 4,749,781, issued Jun. 7, 1988.
48. Szelke, et al., U.S. Pat. No. 4,609,643, issued Sep. 2, 1986.
49. Szelke, et al., U.S. Pat. No. 4,650,661, issued Mar. 17, 1987.
50. Szelke, et al., U.S. Pat. No. 4,713,445, issued Dec. 15, 1987.
51. Thaisrivongs, U.S. Pat. No. 4,705,846, issued Nov. 10, 1987.
52. Hudspeth, et al., U.S. Pat. No. 4,735,933, issued Apr. 5, 1988.
53. Hudspeth, et al., U.S. Pat. No. 4,743,585, issued May 10, 1988.
54. Sham, U.S. Pat. No. 4,826,958, issued May 2, 1989.
55. Rosenberg, et al., U.S. Pat. No. 4,857,507, issued Aug. 15, 1989.
56. Luly, et al., U.S. Pat. No. 4,826,815, issued May 2, 1989.
57. Rosenberg, et al., U.S. Pat. No. 4,837,204, issued Jun. 6, 1989.
58. Luly, et al., U.S. Pat. No. 4,845,079, issued Jul. 4, 1989.
59. Bender, et al., U.S. Pat. No. 4,818,748, issued Apr. 4, 1989.
60. Kleinman, et al., U.S. Pat. No. 4,729,985, issued Mar. 8, 1988.
61. Hoover, et al., U.S. Pat. No. 4,814,342, issued Mar. 21, 1989.
62. Wagnon, et al., U.S. Pat. No. 4,746,648, issued May 24, 1988.
63. Natarajan, et al., U.S. Pat. No. 4,757,050, issued Jul. 12, 1988.
64. Patel, U.S. Pat. No. 4,820,691, issued Apr. 11, 1989.
65. Kaltenbronn, et al., U.S. Pat. No. 4,804,743, issued Feb. 14, 1989.
66. Pinori, et al., U.S. Pat. No. 4,560,505, issued Dec. 24, 1985.
67. Yamato, et al., U.S. Pat. No. 4,683,220, issued Jul. 28, 1987.
68. Boger, et al., U.S. Pat. No. 4,812,442, issued Mar. 14, 1989.
69. Patchett, et al., U.S. Pat. No. 4,839,357, issued Jun. 13, 1989.
70. Boger, et al., U.S. Pat. No. 4,812,442, issued Mar. 14, 1989.
71. Veber, et al., U.S. Pat. No. 4,478,826, issued Oct. 23, 1984.
72. Raddatz, et al., U.S. Pat. No. 4,812,555, issued Mar. 14, 1989.
73. Wagnon, et al., U.S. Pat. No. 4,840,935, issued Jun. 20, 1989.
74. Iizuka, et al., U.S. Pat. No. 4,841,067, issued Jun. 20, 1989.
75. Raddatz, et al., U.S. Pat. No. 4,829,053, issued May 9, 1989.

Preferred renin inhibitors and methods for making them include those disclosed in U.S. Pat. No. 4,826,815, issued May 2, 1989; U.S. Pat. No. 4,857,507, issued Aug. 15, 1989; U.S. Pat. No. 4,826,958, issued May 2, 1989; U.S. Pat. No. 4,837,204, issued Jun. 6, 1989; U.S. Pat. No. 4,845,079 issued Jul. 4, 1989, which are hereby incorporated by reference. Preferred renin inhibitors and methods for making them also include those disclosed in copending U.S. patent applications, U.S. Ser. No. 403,906, filed Sep. 1, 1989; U.S. Ser. No. 231,869, filed Aug. 16, 1988 (EP0307837, published Mar. 22, 1989); U.S. Ser. No. 132,356, filed Dec. 18, 1987 (WO88/05050, published Jul. 14, 1988); PCT/US89/04385, filed Oct. 3, 1989 (WO90/03971, published Apr. 19, 1990); PCT/US89/04649, filed Oct. 18, 1989 (WO90/04917, published May 17, 1990); and U.S. Ser. No. 564,925, filed Aug. 9, 1990 which are hereby incorporated by reference.

The preferred renin inhibiting compounds of this invention are selected from the group consisting of compounds of the formula:

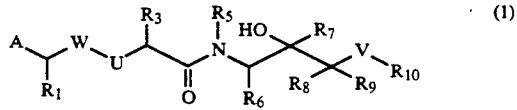 (1)

wherein A is hydrogen, loweralkyl, arylalkyl, —$OR_{20}$ wherein $R_{20}$ is hydrogen, or loweralkyl, —$NR_{21}R_{22}$ wherein $R_{21}$ and $R_{22}$ are independently selected from hydrogen and loweralkyl; or A is

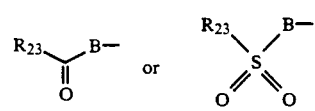

wherein B is NH, O, $CH_2$ or $NHCH_2$; and $R_{23}$ is loweralkyl, alkoxy, arylalkoxy, arylalkoxyalkyl, amino, alkylamino, dialkylamino, carboxyalkyl, alkoxycarbonyalkyl, (dihydroxyalkyl)(alkyl)amino, aminoalkyl, N-protected aminoalkyl, (heterocyclic)alkyl, or a substituted or unsubstituted heterocyclic;

W is C=O, CH$_2$ or CHOH;

U is CH$_2$ or NR2 wherein R$_2$ is hydrogen or loweralkyl, provided that when W is CHOH then U is CH$_2$;

R$_1$ is loweralkyl, cycloalkylakyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or aniline; provided that when R$_1$ is phenoxy, thiophenoxy or anilino, then B is CH$_2$ or A is hydrogen;

R$_3$ is loweralkyl, (thioalkoxy)alkyl, benzyl or heterocyclic ring substituted methyl;

R$_5$ is hydrogen or loweralkyl;

R$_6$ is loweralkyl, cycloalkylmethyl, or benzyl;

R$_7$, R$_8$ and R$_9$ are hydrogen or loweralkyl and may be the same or different; V is NH, O,S,SO,SO$_2$ or CH$_2$;

R$_{10}$ is loweralkyl, cycloalkyl, (cycloalkyl)alkyl, aryl, arylalkyl or an N-protecting group, or V and R$_{10}$ taken together are N$_3$; with the proviso that R$_{10}$ may be an N-protecting group only when V is NH;

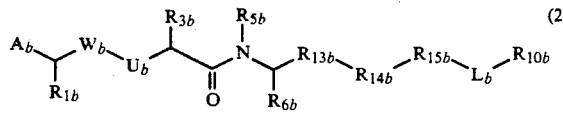
(2)

wherein A$_b$ is hydrogen, loweralkyl, arylalkyl, OR$_{20b}$ or SR$_{20b}$ wherein R$_{20b}$ is hydrogen, loweralkyl or aminoalkyl, NR$_{21b}$ R$_{22b}$ wherein R$_{21b}$ and R$_{22b}$ are independently selected from hydrogen, loweralkyl, aminoalkyl, cyanoalkyl and hydroxyalkyl; or A$_b$ is

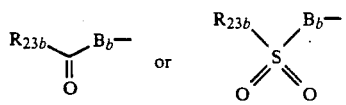

wherein B$_b$ is NH, alkylamino, S, O, CH$_2$ or CHOH; and R$_{23b}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected aminoalkyl, alkylaminoalkyl, carboxyalkyl, alkoxycarbonylalkyl, (N-protected)(alkyl)aminoalkyl, dialkylaminoalkyl, (heterocyclic)alkyl, or a substituted or unsubstituted heterocyclic;

W$_b$ is C=O or CHOH;

U$_b$ is CH$_2$ or NR$_{2b}$ wherein R$_{2b}$ is hydrogen or loweralkyl, provided that when W$_b$ is CHOH then U$_b$ is CH$_2$;

R$_{1b}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or aniline; provided that when R$_{1b}$ is phenoxy, thiophenoxy or anilino, then B$_b$ is CH$_2$ or CHOH or A$_b$ is hydrogen;

R$_{3b}$ is loweralkyl, loweralkenyl, benzyl or heterocyclic ring substituted methyl;

R$_{5b}$ is hydrogen or loweralkyl;

R$_{6b}$ is loweralkyl, cycloalkylmethyl, or benzyl;

R$_{10b}$ is loweralkyl, cycloalkyl, (cycloalkyl)alkyl, aryl, arylalkyl or an N-protecting group, or L$_b$ and R$_{10b}$ taken together can be N$_3$, with the proviso that when L$_6$ is NH then R$_{10b}$ is an N-protecting group;

R$_{13b}$ is CHOH or CO;

R$_{14b}$ is CH$_2$, CF$_2$ or CF with the proviso that when R$_{13b}$ is CO then R$_{14b}$ is CF$_2$;

R$_{15b}$ is CH$_2$, CHR$_{25b}$ wherein R$_{25b}$ is loweralkyl, cycloalkyl, cycloalkylalkyl, aryl or arylalkyl, or R$_{14b}$ and R$_{15b}$ taken together can be

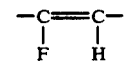

with the proviso that when R$_{14b}$ is CF$_2$ then R$_{15b}$ is CH$_2$;

L$_b$ is O,S,SO,SO$_2$,NR$_{26b}$ wherein R$_{26b}$ is hydrogen or loweralkyl, or NR$_{27b}$ C(O) wherein R$_{27b}$ is hydrogen or loweralkyl;

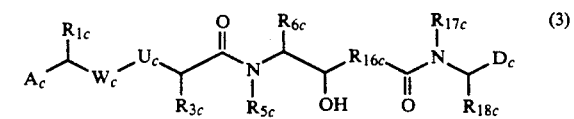
(3)

wherein A$_c$ is 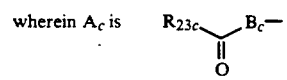

wherein B$_c$ is NH, or CH$_2$; and R$_{23c}$ is loweralkyl, alkoxy, or a substituted or unsubstituted heterocyclic;

W$_c$ is C=O;

U$_c$ is NR$_{2c}$ wherein R$_{2c}$ is hydrogen or loweralkyl;

R$_{1c}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, or phenethyl;

R$_{3c}$ is loweralkyl, benzyl or heterocyclic ring substituted methyl;

R$_{5c}$ is hydrogen or loweralkyl;

R$_{6c}$ is loweralkyl, cycloalkylmethyl, benzyl, or CH$_2$R$_{24c}$ where R$_{24c}$ is selected from 1,3-dioxan-2-yl; 1,3-dioxolan-2-yl, 1,3-dithiolan-2-yl or 1,3-dithian-2-yl;

R$_{16c}$ is CH$_2$, CF$_2$ or CHR$_{63c}$ where R$_{63c}$ is loweralkyl, hydroxy, hydroxyalkyl, alkoxy, allyl, arylalkoxy or thioalkyl;

R$_{17c}$ is hydrogen or loweralkyl;

R$_{18c}$ is loweralkyl or lipophilic or aromatic amino acid side chain;

D$_c$ is hydrogen, loweralkyl or —CH$_2$OR$_{28c}$ wherein R$_{28c}$ is hydrogen, loweralkyl or arylalkyl;

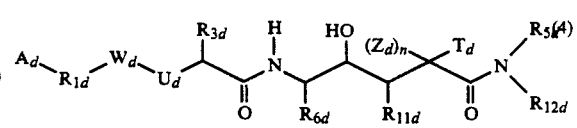

wherein A$_d$ is hydrogen, loweralkyl, arylalkyl, —OR$_{20d}$ or —SR$_{20d}$ wherein R$_{20d}$ is hydrogen, loweralkyl or aminoalkyl, —NR$_{21d}$ R$_{22d}$ wherein R$_{21d}$ and R$_{22d}$ are independently selected from hydrogen, loweralkyl, aminoalkyl, cyanoalkyl and hydroxyalkyl; or A$_d$ is

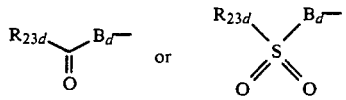

wherein B$_d$ is NH, alkylamino, S, O, CH$_2$ or NHCH$_2$, and R$_{23d}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, ((dialkylamino)alkyl)(alkyl)amino, (dihydroxyalkyl)(alkyl)amino, aminoalkyl, N-protected aminoalkyl, alkylaminoalkyl, carboxyalkyl, alkoxycarbonylalkyl, (N-protected)(alkyl)aminoalkyl, dialkylaminoalkyl, (heterocyclic)alkyl, or a substituted or unsubstituted heterocyclic;

W$_d$ is C=O or CHOH;

U$_d$ is CH$_2$ or NR$_{2d}$ wherein R$_{2d}$ is hydrogen or loweralkyl, provided that when W$_d$ is CHOH then U$_d$ is CH$_2$;

R$_{1d}$ is CHR$_{24d}$ wherein R$_{24d}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazoyl)methyl, (alpha,alpha)-dimethylbenzyl, 1-benzyloxyethyl, or phenethyl, or R$_{1d}$ is C=CHR$_{25d}$ wherein R$_{25d}$ is aryl;

R$_{3d}$ is loweralkyl, alkenyl, benzyl or heterocyclic ring substituted methyl;

R$_{5d}$ is hydrogen or loweralkyl;

R$_{6d}$ is loweralkyl, cycloalkylmethyl, or benzyl;

R$_{11d}$ is hydrogen or hydroxy;

n is 0 or 1; when n is 0 then T$_d$ is alkylidene or alkylidene oxide; and when n is 1 then Z$_d$ is hydrogen or hydroxy and T$_d$ is loweralkyl, hydroxyalkyl, aminoalkyl, haloalkyl, or azidoalkyl;

R$_{12d}$ is hydrogen, loweralkyl, cycloalkylalkyl, arylalkyl, aminoalkyl, or dialkylaminoalkyl;

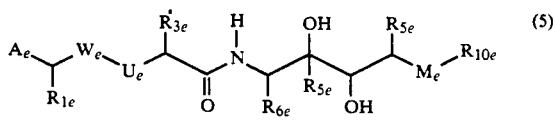

(5)

wherein A$_e$ is hydrogen, loweralkyl, arylalkyl, —OR$_{20e}$ or —SR$_{20e}$ wherein R$_{20e}$ is hydrogen, loweralkyl or aminoalkyl, —NR$_{21e}$R$_{22e}$ wherein R$_{21e}$ and R$_{22e}$ are independently selected from hydrogen, loweralkyl, aminoalkyl, cyanoalkyl and hydroxyalkyl; or A$_e$ is

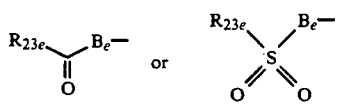

wherein B$_e$ is NH, alkylamino, S, O, CH$_2$ or CHOH; and R$_{23e}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protected aminoalkyl, alkylaminoalkyl, carboxyalkyl, alkoxycarbonylalkyl, (N-protected)(alkyl)aminoalkyl, dialkylaminoalkyl, (heterocyclic)alkyl, or a substituted or unsubstituted heterocyclic;

W$_e$ is C=O;

U$_e$ is NR$_{2e}$ wherein R$_{2e}$ is hydrogen or loweralkyl; R$_{1e}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino, provided that when R$_{1e}$ is phenoxy, thiophenoxy or anilino, then B$_e$ is CH$_2$ or CHOH or A$_e$ is hydrogen;

R$_{3e}$ is loweralkyl, benzyl or heterocyclic ring substituted methyl;

R$_{5e}$ is hydrogen or loweralkyl;

R$_{6e}$ is loweralkyl, cycloalkylmethyl, or benzyl;

M$_e$ is O, NH or S;

R$_{10e}$ is hydrogen, loweralkyl, cycloalkyl, (cycloalkyl)alkyl, aryl, arylalkyl or an N-protecting group;

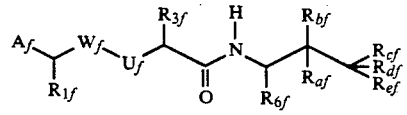

wherein A$_f$ is hydrogen, loweralkyl, arylalkyl, —OR$_{10f}$ or —SR$_{10f}$ wherein R$_{10f}$ is hydrogen, loweralkyl or aminoalkyl, —NR$_{11f}$R$_{12f}$ wherein R$_{11f}$ and R$_{12f}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkyamino)alkoxycarbonylalkyl, ((N-protected)alkylamino)alkoxycarbonylalkyl and (dialkylamino)alkoxycarbonylalkyl; or A$_f$ is

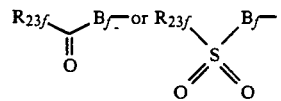

wherein B$_f$ is NH, alkylamino, S, O, CH$_2$ or CHOH and R$_{23f}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, aminoalkyl, N-protectedaminoalkyl, alkylaminoalkyl, (N-protected)(alkyl)aminoalkyl, dialkylaminoalkyl, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, ((N-protected)amino)carboxyalkyl, ((N-protected)amino)carboxyalkylamino, (alkylamino)carboxyalkyl, (alkylamino)carboxyalkylamino, ((N-protected)alkylamino)carboxyalkyl, ((N-protected)alkylamino)carboxyalkylamino, (dialkylamino)carboxyalkyl, (dialkylamino)carboxyalkylamino, (amino)alkoxycarbonylalkyl, (amino)alkoxycarbonylalkylamino, ((N-protected)amino)alkoxycarbonylalkyl, ((N-protected)amino)-alkoxycarbonylalkylamino, (alkylamino)alkoxycarbonylalkyl, (alkylamino)alkoxycarbonylalkylamino, ((N-protected)alkylamino)-alkoxycarbonylalkyl, ((N-protected)alkylamino)alkoxycarbonyl- alkylamino, (dialkylamino)alkoxycarbonylalkyl, (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino, (polyalkyoxy)alkyl(alkyl)amino, di-(alkoxyalkyl)amino, di-(hydroxyalkyl)amino, di-((polyalkoxy)alkyl)amino, polyalkoxy, (polyalkoxy)alkyl, (heterocyclic)alkyl or a substituted or unsubstituted heterocyclic wherein saturated heterocyclics may be unsubstituted, monosubstituted or disubstituted with hydroxy, oxo, amino, alkylamino, dialkylamino, alkoxy, polyalkoxy or loweralkyl; unsaturated heterocyclics may be unsubstituted or monosubstituted with hydroxy, amino, alkylamino, dialkylamino, alkoxy, polyalkoxy or loweralkyl;

$W_f$ is C=O or CHOH;

$U_f$ is $CH_2$ or $NR_{2f}$ provided that when $W_f$ is CHOH then $U_f$ is $CH_2$; $R_{1f}$ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or aniline; provided that when $R_{1f}$ is phenoxy, thiophenoxy or anilino, then $B_f$ is $CH_2$ or CHOH or $A_f$ is hydrogen;

$R_{2f}$ is hydrogen or loweralkyl;

$R_{3f}$ is loweralkyl, loweralkenyl,((alkoxy)alkoxy)loweralkyl, (thioalkoxy)alkyl, benzyl or heterocyclic ring substituted methyl;

$R_{6f}$ is loweralkyl, cycloalkylmethyl or benzyl;

$R_{af}$ is vinyl, formyl, hydroxymethyl or hydrogen;

$R_{df}$ is hydrogen or loweralkyl;

$R_{bf}$ and $R_{ef}$ are independently selected from OH and $NH_2$; and $R_{cf}$ is hydrogen, loweralkyl, vinyl or arylalkyl;

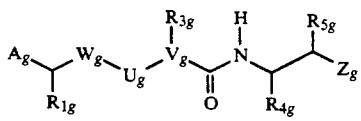  (7)

wherein $A_g$ is hydrogen, loweralkyl, aminoalkyl, (alkyl)aminoalkyl, dialkylaminoalkyl, (alkoxy)aminoalkyl, (alkoxy)(alkyl)aminoalkyl, phenylalkyl, (substituted phenyl)alkyl wherein the phenyl ring is substituted with one, two or three substituents independently selected from loweralkoxy, loweralkyl, amino, alkylamino, dialkylamino, hydroxy, halo, mercapto, nitro, thioalkoxy, carboxaldehyde, carboxy, alkoxycarbonyl and carboxamide, naphthylalkyl, (substituted naphthyl)alkyl wherein the naphthyl ring is substituted with one, two or three substituents independently selected from loweralkoxy, loweralkyl, amino, alkylamino, dialkylamino, hydroxy, halo, mercapto, nitro, thioalkoxy, carboxaldehyde, carboxy, alkoxycarbonyl and carboxamide, substituted or unsubstituted heterocyclic, where saturated heterocyclics may be unsubstituted, monosubstituted or disubstituted with hydroxy, oxo, amino, alkylamino, dialkylamino, alkoxy, polyalkoxy, loweralkyl, haloalkyl or polyhaloalkyl; unsaturated heterocyclics may be unsubstituted or monosubstituted with hydroxy, amino, alkylamino, dialkylamino, alkoxy, polyalkoxy, loweralkyl, haloalkyl or polyhaloalkyl, or $A_9$ is (unsubstituted heterocyclic)alkyl or (substituted heterocyclic)alkyl wherein unsubstituted or substituted heterocyclic is as defined above, or $A_g$ is —$OR_{7g}$ or —$SR_{7g}$ wherein $R_{7g}$ is hydrogen, loweralkyl, aminoalkyl, (alkyl)aminoalkyl, dialkylaminoalkyl, (alkoxy)aminoalkyl, (alkoxy)(alkyl)aminoalkyl, phenylalkyl, (substituted phenyl)alkyl wherein substituted phenyl is as defined above, naphthylalkyl, (substituted naphthyl)alkyl wherein the substituted naphthyl is as defined above, substituted or unsubstituted heterocyclic as defined above, (unsubstituted heterocyclic)alkyl or (substituted heterocyclic)alkyl wherein unsubstituted heterocyclic is as defined above, (unsubstituted heterocyclic)C(O)- or (substituted heterocyclic)C(O)- wherein unsubstituted or substituted heterocyclic is as defined above; or $A_g$ is —$NR_{8g}R_{9g}$ wherein $R_{8g}$ and $R_{9g}$ are independently selected from hydrogen, hydroxy, alkoxy, loweralkyl, aminoalkyl, cyanoalkyl and hydroxyalkyl; or $A_g$ is

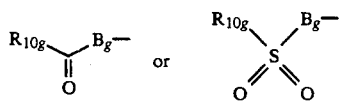

wherein $B_g$ is NH, alkylamino, S, O, $CH_2$, $NHCH_2$ or $CH(OR_{52g})$ wherein $R_{52g}$ is hydrogen, loweralkyl or loweralkylcarbonyl, and $R_{10g}$ is hydrogen, loweralkyl, cycloalkyl, phenyl, substituted phenyl as defined above, naphthyl, substituted naphthyl as defined above, alkoxy, alkenyloxy, hydroxyalkoxy, dihydroxyalkoxy, phenylalkoxy, (substituted phenyl)alkoxy wherein substituted phenyl is as defined above, naphthylalkoxy, (substituted naphthyl)alkoxy wherein substituted naphthyl is as defined above, phenylalkoxyalkyl, (substituted phenyl)alkoxyalkyl wherein substituted phenyl is as defined above, naphthylalkoxyalkyl, (substituted naphthyl)alkoxyalkyl wherein substituted naphthyl is as defined above, thioalkoxyalkyl, loweralkylsulfinylalkyl, loweralkylsulfonylalkyl, phenylthioalkyl, (substituted phenyl)thioalkyl wherein substituted phenyl is as defined above, naphthylthioalkyl, (substituted naphthyl)thioalkyl wherein substituted naphthyl is as defined above, phenylsulfonylalkyl, (substituted phenyl)sulfonylalkyl wherein substituted phenyl is as defined above, naphthylsulfonylalkyl, (substituted naphthyl)sulfonylalkyl wherein substituted naphthyl is as defined above, amino, alkylamino, dialkylamino, (hydroxyalkyl)(alkyl)amino, (dihydroxyalkyl)(alkyl)amino, aminoalkyl, alkoxycarbonylalkyl, carboxyalkyl, (N-protected)aminoalkyl, alkylaminoalkyl, (N-protected)(alkyl)aminoalkyl, dialkylaminoalkyl, (heterocyclic)alkyl, a substituted or unsubstituted heterocyclic as defined above, aminocycloalkyl, aminoalkylamino, (dialkylaminoalkyl)(alkyl)amino, phenylalkylamino, (substituted phenyl)alkylamino wherein substituted phenyl is as defined above, naphthylalkylamino, (substituted naphthyl)alkylamino wherein substituted naphthyl is as defined above, (phenylalkyl)(alkyl)amino, ((substituted phenyl)alkyl)(alkyl)amino wherein substituted phenyl is as defined above, (naphthylalkyl)(alkyl)amino, ((substituted naphthyl)alkyl)amino wherein substituted naphthyl is as defined above, alkoxyalkyl(alkyl)amino, (polyalkoxy)alkyl(alkyl)amino, di-(alkoxyalkyl)amino, di-(hydroxyalkyl)amino, di-((polyalkoxy)alkyl)amino, ((heterocyclic)alkyl)(alkyl)amino, ((heterocyclic)alkyl)amino, (heterocyclic)(alkyl)amino, (alkylaminoalkyl)(alkyl)amino, (dialkylaminoalkyl)(alkyl)amino, ((alkoxy)(alkyl)aminoalkyl)(alkyl)amino, ((alkoxy)aminoalkyl)(alkyl)amino, polyalkoxy or (polyalkoxy)alkyl; or $A_g$ is $R_{41g}CH(OH)CH_2$— or $R_{41g}CH(OH)CH(OH)$— wherein $R_{41g}$ is loweralkyl, cycloalkyl, phenyl, substituted phenyl as defined above, naphthyl, substituted naphthyl as defined above, phenylalkyl, (substituted phenyl)alkyl wherein substituted phenyl is as defined above, naphthylalkyl, (substituted naphthyl)alkyl wherein substituted naphthyl is as defined above, phenylalkoxyalkyl, (substituted phenyl)alkoxyalkyl wherein substituted phenyl is as defined above, naphthylalkoxyalkyl, (substituted naphthyl)alkoxyalkyl wherein substituted naphthyl is as defined above, thioalkoxyalkyl, loweralkylsulfinylalkyl, loweralkylsulfonylalkyl, phenylthioalkyl, (substituted phenyl)thioalkyl wherein substituted phenyl is as defined above, naphthylthioalkyl, (substituted naphthyl)thioalkyl wherein substituted naphthyl is as defined above, phenylsulfonylalkyl, (substituted phenyl)sulfonylalkyl wherein substituted phenyl is as defined above, naphthylsulfonylalkyl, (substituted naphthyl)sulfonylalkyl wherein substituted naphthyl is as defined above, aminoalkyl, alkoxycarbonylalkyl, carboxyalkyl, (N-protected)aminoalkyl, alkylaminoalkyl, (N-protected)(alkyl)aminoalkyl, dialkylaminoalkyl, heterocyclicalkyl, a substituted or unsubstituted heterocyclic as defined above, aminocycloalkyl or (polyalkoxy)alkyl;

$W_g$ is C=O, CHOH or $NR_{2g}$ wherein $R_{2g}$ is hydrogen or loweralkyl;

$U_g$ is C=O, CH$_2$ or $NR_{2g}$ wherein $R_{2g}$ is hydrogen or loweralkyl, with the proviso that when $W_g$ is CHOH then $U_g$ is CH$_2$ and with the proviso that $U_g$ is C=O or CH$_2$ when $W_g$ is $NR_{2g}$;

$V_g$ is CH, C(OH) or C(halogen) with the proviso that $V_g$ is CH when $U_g$ is $NR_{2g}$; $R_{1g}$ is loweralkyl, cycloalkylalkyl, benzyl, (alpha, alpha)-dimethylbenzyl, 4-methoxybenzyl, halobenzyl, 4-hydroxybenzyl, (1-naphthyl)methyl, (2-naphthyl)methyl, (unsubstituted heterocyclic)methyl, (substituted heterocyclic)methyl wherein unsubstituted or substituted heterocyclic is as defined above, phenethyl, 1-benzyloxyethyl, phenoxy, thiophenoxy or anilino, provided that $B_9$ is CH$_2$ or CHOH or $A_g$ is hydrogen when $R_{1g}$ is phenoxy, thiophenoxy or aniline;

$R_{3g}$ is loweralkyl, loweralkenyl, ((alkoxy)alkoxy)alkyl, carboxyalkyl, (thioalkoxy)alkyl, azidoalkyl, aminoalkyl, (alkyl)aminoalkyl, dialkylaminoalkyl, (alkoxy)(alkyl)aminoalkyl, (alkoxy)aminoalkyl, benzyl or heterocyclic ring substituted methyl;

$R_{4g}$ is loweralkyl, cycloalkylmethyl or benzyl;

$R_{5g}$ is OH or NH$_2$; and $Z_g$ is

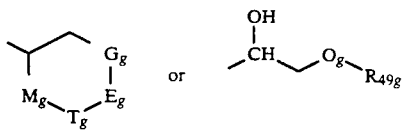

wherein $M_g$ is O, S or NH, $T_g$ is C=O, C=S, S, S(O), S(O)$_2$ or CH$_2$, $E_g$ is O, S, $NR_{6g}$ wherein $R_{6g}$ is hydrogen, loweralkyl, hydroxyalkyl, hydroxy, alkoxy, amino, or alkylamino, or $E_g$ is $CR_{6g}R_{42g}$ wherein $R_{6g}$ is as defined above and $R_{42g}$ is hydrogen or loweralkyl or $E_g$ is C=CR$_{43g}$R$_{44g}$ wherein $R_{43g}$ and $R_{44g}$ are independently selected from hydrogen and loweralkyl, $G_g$ is absent, CH$_2$ or $NR_{11g}$ wherein $R_{11g}$ is hydrogen or loweralkyl, with the proviso that when $G_g$ is $NR_{11g}$ then $R_{6g}$ is loweralkyl or hydroxyalkyl, $Q_g$ is $CR_{45g}R_{46g}$ wherein $R_{45g}$ and $R_{46g}$ are independently selected from hydrogen and loweralkyl or $Q_g$ is C=CR$_{47g}$R$_{48g}$ wherein $R_{47g}$ and $R_{48g}$ are independently selected from hydrogen and loweralkyl, and $R_{49g}$ is —CH$_2$OH, carboxy, alkoxycarbonyl or —CONR$_{50g}$R$_{51g}$ wherein $R_{50g}$ is hydrogen or loweralkyl and $R_{51g}$ is hydrogen, loweralkyl, aminoalkyl, alkylaminoalkyl, dialkylaminoalkyl or alkoxyalkyl;

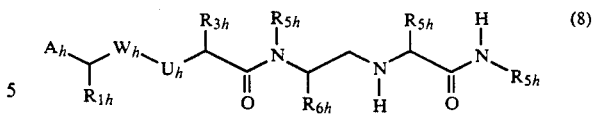

wherein $A_h$ is hydrogen, loweralkyl, arylalkyl, —OR$_{20h}$ or —SR$_{20h}$ wherein R20h is hydrogen, loweralkyl or aminoalkyl, —NR$_{21h}$R$_{22h}$ wherein $R_{21h}$ and $R_{22h}$ are independently selected from hydrogen, loweralkyl, aminoalkyl, cyanoalkyl and hydroxyalkyl; or $A_h$ is

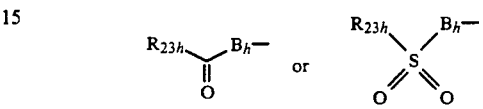

wherein $B_h$ is NH, alkylamino, S, O, CH$_2$ NHCH$_2$ or CHOH; and $R_{23h}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, ((dialkylamino)alkyl)(alkyl)amino, (dihydroxyalkyl)(alkyl)amino, aminoalkyl, N-protected aminoalkyl, alkylaminoalkyl, (N-protected)(alkyl)aminoalkyl, dialkylaminoalkyl, (heterocyclic)alkyl, or a substituted or unsubstituted heterocyclic;

$W_h$ is C=O or CHOH;

$U_h$ is CH$_2$ or $NR_{2h}$ wherein $R_{2h}$ is hydrogen or loweralkyl, provided that when $W_h$ is CHOH then $U_h$ is CH$_2$;

$R_{1h}$ is loweralkyl, cycloalkylalkyl, benzyl, 4-methoxybenzyl, 4-hydroxybenzyl, halobenzyl, (1-naphthyl)methyl, (2-naphthyl)methyl, (4-imidazolyl)methyl, (alpha,alpha)-dimethylbenzyl, 1-benzyloxyethyl, phenethyl, phenoxy, thiophenoxy or anilino, provided that when $R_{1h}$ is phenoxy, thiophenoxy or anilino, then $B_h$ is CH$_2$ or CHOH or $A_h$ is hydrogen;

$R_{3h}$ is loweralkyl, loweralkenyl, ((alkoxy)alkoxy)alkyl, carboxyalkyl, (thioalkoxy)alkyl, benzyl or heterocyclic ring substituted methyl;

$R_{5h}$ is hydrogen or loweralkyl;

$R_{6h}$ is loweralkyl, cycloalkylmethyl, or benzyl;

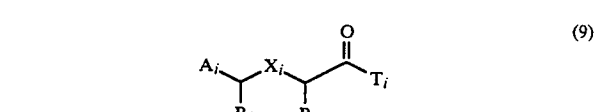

wherein $A_i$ is
(I) $R_{5i}C(O)$—$CH_2)_{w''}$— wherein
 1) w″ is 0 to 4 and
 2) $R_{5i}$ is
  i) hydroxy,
  ii) alkoxy,
  iii) thioalkoxy,
  iv) amino or
  v) substituted amino;
(II) alkylsulfonyl, (aryl)sulfonyl or (heterocyclic)sulfonyl;
(III) aryl, arylalkyl, heterocyclic or (heterocyclic)alkyl; or
(IV) $R_{90i}$— or $R_{90i}$NHC(O)— wherein $R_{90i}$ is a $C_1$ to $C_4$ straight or branched carbon chain substituted by a substituent selected from
 1) carboxy, 2) alkoxycarbonyl,
3) alkylsulfonyl,
4) aryl,
5) arylsulfonyl,
6) heterocyclic or
7) (heterocyclic)sulfonyl);

$R_{1i}$ is
(I) hydrogen
(II) loweralkyl,
(III) loweralkenyl,
(IV) cycloalkylalkyl,
(V) cycloalkenylalkyl,
(VI) aryloxyalkyl,
(VII) thioaryloxyalkyl,
(IV) arylalkoxyalkyl,
(IX) arylthioalkoxyalkyl or
(X) a $C_1$ to $C_3$ straight or branched carbon chain substituted by a substituent selected from
  1) alkoxy,
  2) thioalkoxy,
  3) aryl and
  4) heterocyclic;

X is
(I) $CH_2$,
(II) CHOH,
(III) C(O),
(IV) O,
(VI) S,
(VII) S(O),
(VIII) $SO_2$,
(IX) N(O) or
(X) —P(O)—;

$R_{3i}$ is
(I) loweralkyl,
(II) haloalkyl,
(III) loweralkenyl,
(IV) cycloalkylalkyl,
(V) cycloalkenylalkyl,
(VI) alkoxyalkyl,
(VII) thioalkoxyalkyl,
(VIII) (alkoxyalkoxy)alkyl,
(IX) hydroxyalkyl,
(X) —$(CH_2)_{ee}NHR_{12i}$ wherein
  1) ee is 1 to 3 and
  2) $R_{12i}$ is
    i) hydrogen,
    ii) loweralkyl or
    iii) an N-protecting group;
(XI) arylalkyl or
(XII) (heterocyclic)alkyl; and $T_i$ is

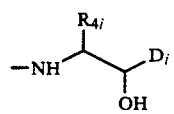

wherein $R_{4i}$ is
(I) loweralkyl,
(II) cycloalkylalkyl
(III) cycloalkenylalkyl or
(IV) arylalkyl; and
$D_i$ is

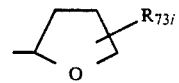

(I)

wherein $R_{73i}$ is loweralkyl,

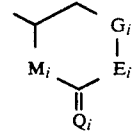

(II)

wherein
1) $M_i$ is
  i) O,
  ii) S or
  iii) NH;
2) $Q_i$ is
  i) O or
  ii) S;
3) $E_i$ is
  i) O,
  ii) S,
  iii) $CHR_{73i}$ wherein $R_{73i}$ is loweralkyl,
  iv) $C=CH_2$ or
  v) $NR_{18i}$ wherein $R_{18i}$ is
    a) hydrogen,
    b) loweralkyl,
    c) hydroxyalkyl,
    d) hydroxy,
    e) alkoxy,
    f) amino or
    g) alkylamino;
and
4) $G_i$ is
  i) absent,
  ii) $CH_2$ or
  iii) $NR_{19i}$ wherein $R_{19i}$ is hydrogen or loweralkyl, with the proviso that when $G_i$ is $NR_{19i}$, then $R_{18i}$ is loweralkyl or hydroxyalkyl;

(III)

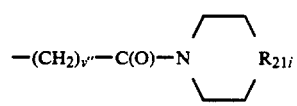

(III)

wherein
1) v" is 0 or 1 and
2) $R_{21i}$ is
  i) NH,
  ii) O,
  iii) S or
  iv) $SO_2$; or
(IV) a substituted methylene group; and (10).

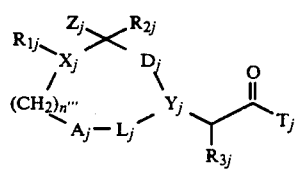

(10).

wherein $X_j$ is (I) N,
(II) O or
(III) CH;
$R_{1j}$ is
(I) absent,
(II) hydrogen,
(III) an N-protecting group,
(IV) aryl,
(V) heterocyclic, or
(VI) $R_{6j}$—Q— wherein
  1) $R_{6j}$ is
    i) loweralkyl,
    ii) amino,
    iii) alkylamino,
    iv) dialkylamino,
    v) (alkoxyalkyl)(alkyl)amino,
    vi) (alkoxyalkoxyalkyl)(alkyl)amino,
    vii) aryl,
    viii) arylalkyl,
    ix) aminoalkyl,
    x) (N-protected)aminoalkyl,
    xi) alkoxy,
    xii) substituted loweralkyl wherein the substituent is selected from alkoxy, thioalkoxy, halogen, alkylamino, (N-protected)(alkyl)amino and dialkylamino, xiii) 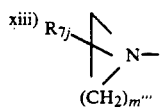

wherein m''' is 1 to 5 and $R_{7j}$ is hydrogen, hydroxy, alkoxy, thioalkoxy, alkoxyalkoxy, polyalkoxy, amino, (N-protected)amino, alkylamino, (N-protected)(alkyl)amino or dialkylamino; or xiv) 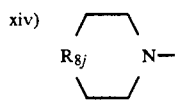

wherein $R_{8j}$ is O, S, SO$_2$, O=C or $R_{9j}$N wherein $R_{9j}$ is hydrogen, loweralkyl or an N-protecting group; and
  2) $Q_j$ is
    i) C=O or
    ii) CH$_2$'
    with the proviso that $X_j$ is N when $R_{1j}$ is an N-protecting group;
(VII) $R_{54j}$S(O)$_2$— wherein $R_{54j}$ is
  1) amino
  2) alkylamino,
  3) dialkylamino,
  4) loweralkyl,
  5) haloalkyl,
  6) aryl,
  7) p-biphenyl,
  8) heterocyclic or
(VIII) $(R_{55j})_2$P(O)— wherein $R_{55j}$ is
  1) alkoxy,
  2) alkylamino or
  3) dialkylamino;
$A_j$ and $L_j$ are independently selected from
(I) absent,
(II) C=O,
(III) SO$_2$ and
(IV) CH$_2$;
$D_j$ is
(I) C=O,
(II) SO$_2$ or
(III) CH$_2$;
$Y_j$ is
(I) N or
(II) CH;
$R_{2j}$ is
(I) hydrogen,
(II) loweralkyl,
(III) cycloalkylalkyl,
(IV) —CH$_2$—$R_{10j}$—(CH$_2$)$_{q'''}$—$R_{11j}$ wherein
  1) q''' is 0, 1 or 2,
  2) $R_{10j}$ is absent or $R_{10j}$ is O, NH or S only when q''' is 1 or 2, and
  3) $R_{11j}$ is
    i) aryl or
    ii) heterocyclic;
$Z_j$ is
(I) hydrogen or
(II) —$R_{28j}$C(O)$R_{29j}$—$_{28j}$S(O)$_2$R$_{29j}$ or —$R_{28j}$C(S)$R_{29j}$ wherein
  1) $R_{28j}$ is
    i) NH,
    ii) —N($R_{200j}$)— wherein $R_{200j}$ is is loweralkyl or benzyl or
    iii) CH$_2$ and
  2) $R_{29j}$ is
    i) alkoxy,
    ii) benzyloxy,
    iii) alkylamino,
    iv) dialkylamino,
    v) aryl or
    vi) heterocyclic;
$R_{3j}$ is
(I) hydrogen,
(II) loweralkyl,
(III) loweralkenyl,
(IV) cycloalkylalkyl,
(V) cycloalkenylalkyl,
(VI) alkoxyalkyl
(VII) thioalkoxyalkyl,
(VIII) (alkoxyalkoxy)alkyl,
(IX) (polyalkoxy)alkyl,
(X) arylalkyl or
(XI) (heterocyclic)alkyl;
n''' is 0 or 1; and
$T_j$ is

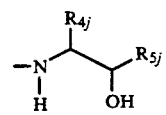

wherein $R_{4j}$ is
(I) loweralkyl,
(II) cycloalkylalkyl or
(III) arylalkyl; and
$R_{5j}$ is

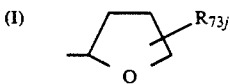

wherein R$_{73j}$ is loweralkyl,

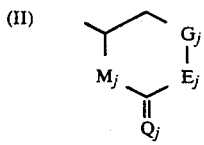

wherein
1) M$_j$ is
  i) O
  ii) S or
  iii) NH;
2) O$_j$ is
  i) O or
  ii) S;
3) E$_j$ is
  i) O,
  ii) S,
  iii) CHR$_{61j}$ wherein R$_{61j}$ is loweralkyl,
  iv) C=CH$_2$ or
  v) NR$_{18j}$ wherein R$_{18j}$ is
    a) hydrogen,
    b) loweralkyl
    c) hydroxyalkyl,
    d) hydroxy,
    e) alkoxy,
    f) amino or
    g) alkylamino;
and
4) G$_j$ is
  i) absent,
  ii) CH$_2$ or
  iii) NR$_{19j}$ wherein R$_{19j}$ is hydrogen or loweralkyl, with the proviso that when G$_j$ is NR$_{19j}$, then R$_{18j}$ is loweralkyl or hydroxyalkyl;

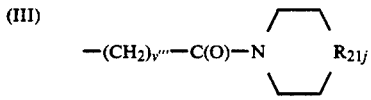

wherein
1) v''' is 0 or 1 and
2) R$_{21j}$ is
  i) NH,
  ii) O,
  iii) S or
  iv) SO$_2$; or (IV) a substituted methylene group; or a pharmaceutically acceptable salt, ester or prodrug thereof.

The term "loweralkyl" as used herein refers to straight or branched chain alkyl radicals containing from 1 to 7 carbon atoms including but not limited to methyl, ethyl, n-propyl, iso-propyl, n-butyl, iso-butyl, sec-butyl, n-pentyl, 2-methylbutyl, 2,2-dimethylpropyl, n-hexyl, 2-methyl-pentyl, 2,2-dimethylbutyl, n-heptyl, 2-methylhexyl and the like.

The term "loweralkenyl" as used herein refers to a straight or branched chain loweralkyl radical which contains at least one carbon-carbon double bond.

The term "cycloalkyl" as used herein refers to an aliphatic ring having 3 to 7 carbon atoms.

The term "cycloalkylalkyl" as used herein refers to a cycloalkyl residue appended to a loweralkyl radical and includes but is not limited to cyclohexylmethyl and cyclopentylmethyl.

The term "cycloalkenyl" as used herein refers to an aliphatic ring having 3–7 carbon atoms and also having at least one carbon-carbon double bond including, but not limited to, cyclohexenyl and the like.

The term "cycloalkenylalkyl" as used herein refers to a cycloalkenyl group appended to a loweralkyl radical including, but not limited to, cyclohexenylmethyl, cyclopentenylethyl and the like.

The term "arylalkyl" as used herein refers to an aryl group as defined herein appended to a loweralkyl radical including but not limited to benzyl, 1- and 2-naphthylmethyl, halobenzyl, and alkoxybenzyl.

The term "phenylalkyl" as used herein refers to a phenyl group appended to a loweralkyl radical, including, but not limited to benzyl, phenethyl and the like.

The term "(substituted phenyl)alkyl" as used herein refers to a substituted phenyl group appended to a loweralkyl radical wherein the phenyl ring is substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halobenzyl, alkoxybenzyl and the like.

The term "naphthylalkyl" as used herein refers to a naphthyl group appended to a loweralkyl radical, including, but not limited to 1-naphthylmethyl, 2-naphthylmethyl and the like.

The term "(substituted naphthyl)alkyl" as used herein refers to a substituted naphthyl group appended to a loweralkyl radical wherein the naphthyl ring is substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halonaphthylmethyl, alkoxynaphthylmethyl and the like.

The term "(heterocyclic)alkyl" as used herein refers to an unsubstituted or substituted heterocyclic ring as defined below appended to a loweralkyl radical, including, but not limited to imidazolylmethyl, thiazolylmethyl and the like.

The term "hydroxyalkyl" as used herein refers to —OH appended to a loweralkyl radical.

The term "alkoxyalkyl" as used herein refers to an alkoxy group appended to a loweralkyl radical.

The term "arylalkoxyalkyl" as used herein refers to an arylalkoxy appended to a loweralkyl radical.

The term "phenylalkoxyalkyl" as used herein refers to a phenylalkoxy group appended to a loweralkyl radical, including, but not limited to phenylmethoxymethyl and the like.

The term "(substituted phenyl)alkoxyalkyl" as used herein refers to a (substituted phenyl)alkoxy group appended to a loweralkyl radical, including, but not limited to 4-chlorophenylmethoxymethyl.

The term "naphthylalkoxyalkyl" as used herein refers to a naphthylalkoxy group appended to a loweralkyl radical, including, but not limited to 1-naphthylmethoxymethyl and the like.

The term "(substituted naphthyl)alkoxyalkyl" as used herein refers to a (substituted naphthyl)alkoxy group appended to a loweralky radical, including, but not limited to halonaphthylmethoxymethyl and the like.

The term "thioalkoxyalkyl" as used herein refers to a thioalkoxy group appended to a loweralkyl radical.

The term "((alkoxy)alkoxy)alkyl" as used herein refers to an alkoxy group appended to an alkoxy group which is appended to a loweralkyl radical, including, but not limited to methoxymethoxymethyl and the like.

The term "polyalkoxyalkyl" as used herein refers to a polyalkoxy residue appended to a loweralkyl radical, including, but not limited to methoxyethoxymethoxymethyl and the like.

The term "aminoalkyl" as used herein refers to $-NH_2$ appended to a loweralkyl radical.

The term "alkylaminoalkyl" as used herein refers to $-NHR_{70}$ appended to a loweralkyl radical, wherein $R_{70}$ is a loweralkyl radical.

The term "dialkylaminoalkyl" as used herein refers to a dialkylamino appended to a loweralkyl radical.

The term "aminocycloalkyl" as used herein refers to an $-NH_2$ appended to a cycloalkyl radical.

The term "N-protected aminoalkyl" as used herein refers to $-NHR_{71}$ appended to a loweralkyl group, wherein $R_{71}$ is an N-protecting group.

The term "(N-protected)(alkyl)amino alkyl" as used herein refers to $-NR_{71}R_{72}$ which is appended to a loweralkyl radical, wherein $R_{71}$ is defined as above and $R_{72}$ is a loweralkyl group.

The term "alkoxycarbonylalkyl" as used herein refers to $R_{73}C(O)R_{74}$— wherein $R_{73}$ is an alkoxy group and $R_{74}$ is a loweralkyl radical.

The term "carboxyalkyl" as used herein refers to a carboxylic acid group (—COOH) appended to a loweralkyl radical.

The term "cyanoalkyl" as used herein refers to —CN appended to a loweralkyl radical.

The term "azidoalkyl" as used herein refers to $-N_3$ appended to a loweralkyl radical.

The term "(alkoxy)aminoalkyl" as used herein refers to an alkoxy group appended to an amino group which in turn is appended to a loweralkyl radical.

The term "(alkoxy)(alkyl)aminoalkyl" as used herein refers to an $-NR_{75}R_{76}$ group appended to a loweralkyl radical wherein $R_{75}$ is an alkoxy group and $R_{76}$ is a loweralkyl group.

The term "loweralkylsulfinylalkyl" as used herein refers to a $R_{77}S(O)$— group appended to a loweralkyl radical wherein $R_{77}$ is a loweralkyl group.

The term "loweralkylsulfonylalkyl" as used herein refers to a $R_{78}S(O)_2$— group appended to a loweralkyl radical wherein $R_{78}$ is a loweralkyl group.

The term "phenylthioalkyl" as used herein refers to a $R_{79}S$— group appended to a loweralkyl radical wherein $R_{79}$ is a phenyl group.

The term "(substituted phenyl)thioalkyl" as used herein refers to a $R_{80}S$— group appended to a loweralkyl radical wherein $R_{80}$ is a substituted phenyl group.

The term "naphthyl thioalkyl" as used herein refers to a $R_{81}S$— group appended to a loweralkyl radical wherein $R_{81}$ is a naphthyl group.

The term "(substituted naphthyl)thioalkyl" as used herein refers to a $R_{82}S$— group appended to a loweralkyl radical wherein $R_{82}$ is a substituted naphthyl group.

The term "phenylsulfonylalkyl" as used herein refers to a $R_{83}S(O)_2$— group appended to a loweralkyl radical wherein $R_{83}$ is a phenyl group.

The term "(substituted phenyl)sulfonylalkyl" as used herein refers to a $R_{84}S(O)_2$— group appended to a loweralkyl radical wherein $R_{84}$ is a substituted phenyl group.

The term "naphthylsulfonylalkyl" as used herein refers to a $R_{85}S(O)_2$— group appended to a loweralkyl group wherein $R_{85}$ is a naphthyl group.

The term "(substituted naphthyl)sulfonylalkyl" as used herein refers to a $R_{86}S(O)_2$— group appended to a loweralkyl group wherein $R_{86}$ is a substituted naphthyl group.

The term "carboxyalkoxyalkyl" as used herein refers to a carboxylic acid group (—COOH) appended to an alkoxy group which is appended to a loweralkyl radical.

The term "alkoxycarbonylalkoxyalkyl" as used herein refers to an alkoxycarbonyl group ($R_{87}CO$— wherein $R_{87}$ is an alkoxy group) appended to an alkoxy group which is appended to a loweralkyl radical.

The term "(amino)carboxyalkyl" as used herein refers to a loweralkyl radical to which is appended a carboxylic acid group (—COOH) and an amino group ($-NH_2$).

The term "((N-protected)amino)carboxyalkyl" as used herein refers to a loweralkyl radical to which is appended a carboxylic acid group (—COOH) and $-NHR_{88}$ wherein $R_{88}$ is an N-protecting group.

The term "(alkylamino)carboxyalkyl" as used herein refers to a loweralkyl radical to which is appended a carboxylic acid group (—COOH) and an alkylamino group.

The term "((N-protected)alkylamino)-carboxyalkyl" as used herein refers to a loweralkyl radical to which is appended a carboxylic acid group (—COOH) and an $-NR_{89}R_{90}$ wherein $R_{89}$ is as defined above and $R_{90}$ is a loweralkyl group.

The term "(dialkylamino)carboxyalkyl" as used herein refers to a loweralkyl radical to which is appended a carboxylic acid group (—COOH) and $-NR_{91}R_{92}$ wherein $R_{91}$ and $R_{92}$ are independently selected from loweralkyl.

The term "(amino)alkoxycarbonylalkyl" as used herein refers to a loweralkyl radical to which is appended an alkoxycarbonyl group as defined above and an amino group ($-NH_2$).

The term "((N-protected)amino)alkoxycarbonylalkyl" as used herein refers to a loweralkyl radical to which is appended an alkoxycarbonyl group as defined above and $-NHR_{93}$ wherein $R_{93}$ is as defined above.

The term "(alkylamino)alkoxycarbonylalkyl" as used herein refers to a loweralkyl radical to which is appended an alkoxycarbonyl group as defined above and an alkylamino group as defined above.

The term "((N-protected)alkylamino)alkoxycarbonylalkyl" as used herein refers to a loweralkyl radical to which is appended an alkoxycarbonyl group as defined above and $-NR_{94}R_{95}$ wherein $R_{94}$ is an N-protecting group and $R_{95}$ is a loweralkyl group.

The term "(dialkylamino)alkoxycarbonylalkyl" as used herein refers to a loweralkyl radical to which is appended an alkoxycarbonyl group as defined above and $-NR_{96}R_{97}$ wherein $R_{96}$ and $R_{97}$ are independently selected from loweralkyl.

The term "carboxyalkylamino" as used herein refers to $-NRH_{98}$ wherein $R_{98}$ is a carboxyalkyl group.

The term "alkoxycarbonylalkylamino" as used herein refers to —NHR$_{99}$ wherein R$_{99}$ is an alkoxycarbonylalkyl group.

The term "(amino)carboxyalkylamino" as used herein refers to —NHR$_{100}$ wherein R$_{100}$ is an (amino)carboxyalkyl group.

The term "((N-protected)amino)carboxyalkylamino" as used herein refers to —NHR$_{101}$ wherein R$_{101}$ is an ((N-protected)amino)carboxyalkyl group.

The term "(alkylamino)carboxyalkylamino" as used herein refers to —NHR$_{102}$ wherein R$_{102}$ is an (alkylamino)carboxyalkyl group.

The term "((N-protected)alkylamino)-carboxyalkylamino" as used herein refers to —NHR$_{103}$ wherein R$_{103}$ is an ((N-protected)alkylamino)carboxyalkyl group.

The term "(dialkylamino)carboxyalkylamino" as used herein refers to —NHR$_{104}$ wherein R$_{104}$ is a (dialkylamino)carboxyalkyl group.

The term "(amino)alkoxycarbonylalkylamino" as used herein refers to —NHR$_{105}$ wherein R$_{105}$ is an (amino)alkoxycarbonylalkyl group.

The term "((N-protected)amino)alkoxycarbonylalkylamino" as used herein refers to —NHR$_{106}$ wherein R$_{106}$ is an ((N-protected)amino)alkoxycarbonylalkyl group.

The term "(alkylamino)alkoxycarbonylalkylamino" as used herein refers to —NHR$_{107}$ wherein R$_{107}$ is an (alkylamino)alkoxycarbonylalkyl group.

The term "((N-protected)alkylamino)alkoxycarbonylalkylamino" as used herein refers to —NHR$_{108}$ wherein R$_{108}$ is an ((N-protected)alkylamino)alkoxycarbonylalkyl group.

The term "(dialkylamino)alkoxycarbonylalkylamino" as used herein refers to —NHR$_{109}$ wherein R$_{109}$ is a (dialkylamino)alkoxycarbonylalkyl group.

The term "alkylidene" as used herein refers to a straight or branched chain alkyl radical which is attached via a carbon-carbon double bond and includes but is not limited to methylidene, ethylidene, 1-propylidene, 1-butylidene, 1-pentylidene, 2-propylidene, 2-butylidene, 2-pentylidene, 3-pentylidene, 3-hexylidene, 3-heptylidene and 4-heptylidene.

The term "alkylidene oxide" as used herein refers to an epoxide moiety which is derived from an alkylidene group.

The term "amino" as used herein refers to an —NH$_2$ substituent.

The term "alkylamino" as used herein refers to —NHR$_{110}$, wherein R$_{110}$ is a loweralkyl group.

The term "dialkylamino" as used herein refers to —NR$_{111}$R$_{112}$ wherein R$_{111}$ and R$_{112}$ are independently selected from loweralkyl groups.

The term "arylalkylamino" as used herein refers to R$_{113}$NH—, wherein R$_{113}$ is an arylalkyl residue.

The term "arylalkyl(alkyl)amino" as used herein refers to R$_{114}$R$_{115}$N—, wherein R$_{114}$ is an arylalkyl residue and R$_{115}$ is a loweralkyl residue.

The term "phenylalkylamino" as used herein refers to a phenylalkyl group appended to an amino radical, including, but not limited to benzylamino and the like.

The term "(substituted phenyl)alkylamino" as used herein refers to a (substituted phenyl)alkyl group appended to an amino radical, including, but not limited to 4-chlorobenzylamino and the like.

The term "napthylalkylamino" as used herein refers to a naphthylalkyl group appended to an amino radical, including, but not limited to 1-naphthylmethylamino and the like.

The term "(substituted naphthyl)alkylamino" as used herein refers to a (substituted naphthyl)alkyl group appended to an amino radical.

The term "(phenylalkyl)(alkyl)amino" as used herein refers to R$_{116}$R$_{117}$N—, wherein R$_{116}$ is a phenylalkyl residue and R$_{117}$ is a loweralkyl residue.

The term "((substituted phenyl)alkyl)-(alkyl)amino" as used herein refers to R$_{118}$R$_{119}$N— wherein R$_{118}$ is a (substituted phenyl)alkyl group and R$_{119}$ is a loweralkyl group.

The term "(naphthylalkyl)(alkyl)amino" as used herein refers to R$_{120}$R$_{121}$N— wherein R$_{120}$ is a naphthylalkyl group and R$_{121}$ is a loweralkyl group.

The term "((substituted naphthyl)alkyl)(alkyl)amino" as used herein refers to R$_{122}$R$_{123}$N— wherein R$_{122}$ is a (substituted naphthyl)alkyl group and R$_{123}$ is a loweralkyl group.

The term "aminoalkylamino" as used herein refers to R$_{124}$NH— where R$_{124}$ is an aminoalkyl residue.

The term "dialkylamino(alkyl)amino" as used herein refers to R$_{125}$R$_{126}$N—, wherein R$_{125}$ is a dialkylamino residue appended to a loweralkyl residue and R$_{126}$ is a loweralkyl residue.

The term "((dialkylamino)alkyl)(alkyl)amino" as used herein refers to —NR$_{127}$R$_{128}$ wherein R$_{127}$ is a dialkylamino residue appended to a loweralkyl residue and R$_{128}$ is a loweralkyl residue.

The term "(hydroxyalkyl)(alkyl)amino" as used herein refers to —NR$_{129}$R$_{130}$ wherein R$_{129}$ is a hydroxyalkyl group and R$_{130}$ is a loweralkyl group.

The term "(di-hydroxyalkyl)(alkyl)amino" as used herein refers to a loweralkyl group which is disubstituted with —OH radicals appended to an amino group, which amino group also has appended another loweralkyl group.

The term "di-(hydroxyalkyl)amino" as used herein refers to R$_{131}$R$_{132}$N—, wherein R$_{131}$ and R$_{132}$ are hydroxyalkyl residues.

The term "alkoxyalkyl(alkyl)amino" as used herein refers to R$_{133}$R$_{134}$N—, wherein R$_{133}$ is a loweralkyl group and R$_{134}$ is an alkoxyalkyl group.

The term "di-(alkoxyalkyl)amino" as used herein refers to R$_{135}$R$_{136}$N—, wherein R$_{135}$ and R$_{136}$ are alkoxy residues appended to loweralkyl residues.

The term "di-(polyalkoxyalkyl)amino" as used herein refers to R$_{137}$R$_{138}$N—, wherein R$_{137}$ and R$_{138}$ are polyalkoxy residues appended to loweralkyl residues.

The term "((polyalkoxy)alkyl)(alkyl)amino" as used herein refers to R$_{139}$R$_{140}$N—, wherein R$_{139}$ is a polyalkoxy residue appended to a loweralkyl radical and R$_{140}$ is a loweralkyl residue.

The term "((heterocyclic)alkyl)(alkyl)amino" as used herein refers to —NR$_{141}$R$_{142}$ wherein R$_{141}$ is a heterocyclicalkyl group and R$_{142}$ is a loweralkyl group.

The term "(heterocyclicalkyl)amino" as used herein refers to —NHR$_{143}$ wherein R$_{143}$ is a heterocyclic alkyl group.

The term "(heterocyclic)(alkyl)amino" as used herein refers to —NR$_{144}$R$_{145}$ wherein R$_{144}$ is a substituted or unsubstituted heterocyclic group and R$_{145}$ is a loweralkyl group.

The term "(alkylaminoalkyl)(alkyl)amino" as used herein refers to —NR$_{146}$R$_{147}$ wherein R$_{146}$ is an alkylaminoalkyl group and R$_{147}$ is a loweralkyl group.

The term "(dialkylaminoalkyl)(alkyl)amino" as used herein refers to $-NR_{148}R_{149}$ wherein $R_{148}$ is a dialkylaminoalkyl group and $R_{149}$ is a loweralkyl group.

The term "((alkoxy)(alkyl)aminoalkyl)-(alkyl)amino" as used herein refers to $-NR_{150}R_{151}$ wherein $R_{150}$ is $-NR_{152}R_{153}$ appended to a loweralkyl radical wherein $R_{152}$ is an alkoxy group and $R_{153}$ is a loweralkyl group and $R_{151}$ is a loweralkyl group.

The term "((alkoxy)aminoalkyl)(alkyl)amino" as used herein refers to $-NR_{154}R_{155}$ wherein $R_{154}$ is $-NHR_{156}$ appended to a loweralkyl group and wherein $R_{156}$ is an alkoxy group and $R_{155}$ is a loweralkyl group.

The term "(alkoxyalkoxyalkyl)(alkyl)amino" as used herein refers to $-NR_{305}R_{306}$ wherein $R_{305}$ is an alkoxyalkoxyalkyl group and $R_{306}$ is a loweralkyl group.

The term "di(alkoxyalkoxyalkyl)amino" as used herein refers to $-NR_{307}R_{308}$ wherein $R_{307}$ and $R_{308}$ are alkoxyalkoxyalkyl groups.

The term "alkylsulfonylamino" as used herein refers to $R_{309}NH-$ wherein $R_{309}$ is an alkylsulfonyl group.

The term "arylsulfonylamino" as used herein refers to $R_{310}NH-$ wherein $R_{310}$ is an arylsulfonyl group.

The term "alkylaminocarbonylamino" as used herein refers to $R_{311}C(O)NH-$ wherein $R_{311}$ is an alkylamino group.

The term "alkylaminocarbonyloxy" as used herein refers to $R_{312}C(O)O-$ wherein $R_{312}$ is an alkylamino group.

The term "alkoxycarbonyloxy" as used herein refers to $R_{313}C(O)O-$ wherein $R_{313}$ is an alkoxy group.

The term "loweralkylcarbonyl" as used herein refers to $R_{157}C(O)-$ wherein $R_{157}$ is a loweralkyl group, including, but not limited to acetyl, propionyl and the like.

The terms "alkoxy" and "thioalkoxy" as used herein refer to $R_{158}O-$ and $R_{158}S-$, respectively, wherein $R_{158}$ is a loweralkyl group.

The term "alkoxyalkoxy" as used herein refers to an alkoxy group appended to an alkoxy radical including, but not limited to, methoxymethoxy and the like.

The term "aryloxyalkyl" as used herein refers to an aryloxy group ($R_{303}O-$ wherein $R_{303}$ is an aryl group) appended to a loweralkyl radical.

The term "thioaryloxyalkyl" as used herein refers to a thioaryloxy group ($R_{304}S-$ wherein $R_{304}$ is an aryl group) appended to a loweralkyl radical.

The terms "arylalkoxy" and "arylthioalkoxy" as used herein refer to an aryl group appended to an alkoxy radical or a thioalkoxy radical, respectively, including, but not limited to, phenoxymethyl, thiophenoxymethyl and the like.

The terms "arylalkoxyalkyl" and arylthioalkoxyalkyl" as used herein refer to an arylalkoxy group or an arylthioalkoxy group, respectively, appended to a loweralkyl radical.

The term "alkenyloxy" as used herein refers to $R_{159}O-$, wherein $R_{159}$ is an alkyl group of 1 to 7 carbon atoms which contains at least one carbon-carbon double bond.

The term "hydroxyalkoxy" as used herein refers to $-OH$ appended to an alkoxy radical.

The term "dihydroxyalkoxy" as used herein refers to an alkoxy radical which is disubstituted with $-OH$ radicals.

The term "arylalkoxy" as used herein refers to an aryl group appended to an alkoxy radical.

The term "alkylaryloxy" as used herein refers to $R_{160}O-$ wherein $R_{160}$ is an alkylaryl group.

The term "phenylalkoxy" as used herein refers to a phenyl group appended to an alkoxy radical, including, but not limited to benzyloxy and the like.

The term "(substituted phenyl)alkoxy" as used herein refers to a substituted phenyl group appended to an alkoxy radical, including, but not limited to 4-chlorobenzyloxy and the like.

The term "naphthylalkoxy" as used herein refers to a naphthyl group appended to an alkoxy radical.

The term "(substituted naphthyl)alkoxy" as used herein refers to a substituted naphthyl group appended to an alkoxy radical.

The term "polyalkoxy" as used herein refers to $R_{161}O-$, wherein $R_{161}$ is a straight or branched chain containing 1-5, $C_m-O-C_{m'}$, linkages where m and m' are independently 1 to 3.

The terms "halo" or "halogen" as used herein refer to Cl, Br, F or I substituents.

The term "haloalkyl" as used herein refers to a loweralkyl radical in which one or more hydrogen atoms are replaced by halogen including, but not limited to fluoromethyl, 2-chloroethyl, trifluoromethyl, 2,2-dichloroethyl and the like.

The term "polyhaloalkyl" as used herein refers to a loweralkyl radical substituted with two or more halogens, including, but not limited to trifluoromethyl, 2,2-dichloroethyl and the like.

The term "halobenzyl" as used herein refers to a halo substituent appended to the phenyl ring of a benzyl radical.

The term "halophenyl" as used herein refers to a halo substituent appended to a phenyl radical.

The term "alkylsulfonyl" as used herein refers to $R_{300}S(O)_2-$ wherein $R_{300}$ is a loweralkyl group.

The term "(aryl)sulfonyl" as used herein refers to $R_{301}S(O)_2-$ wherein $R_{301}$ is an aryl group.

The term "(heterocyclic)sulfonyl" as used herein refers to $R_{302}S(O)_2-$ wherein $R_{302}$ is a heterocyclic group.

The term "arylsulfonylalkyl" as used herein refers to an arylsulfonyl group appended to a loweralkyl radical.

The term "aryl" as used herein refers to a monocyclic or bicyclic carbocyclic ring system having one or more aromatic rings including, but not limited to, phenyl, naphthyl, tetrahydronaphthyl, indanyl and the like; or "aryl" refers to a heterocyclic aromatic ring as defined herein. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "substituted phenyl" as used herein refers to a phenyl ring substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halophenyl, loweralkylphenyl, alkoxyphenyl and the like.

The term "substituted naphthyl" as used herein refers to a naphthyl ring substituted with one, two or three substituents chosen from the group loweralkoxy, loweralkyl, amino, loweralkylamino, hydroxy, halo, mercapto, nitro, thioalkoxy, carboxaldehyde, carboxy, carboalkoxy and carboxamide, including, but not limited to halonaphthyl, alkoxynaphthyl and the like.

The term "alkylaryl" as used herein refers to a loweralkyl group appended to an aryl radical.

The term "heterocyclic group" or "heterocyclic" as used herein refers to any 3- or 4-membered ring containing a heteroatom selected from oxygen, sulfur and nitrogen, or a 5- or 6-membered ring containing from one to three nitrogen atoms; or one nitrogen and one oxygen atom; or one nitrogen and one sulfur atom; wherein the 5-membered ring has 0 to 2 double bonds and the 6-membered ring has 0 to 3 double bonds; wherein the nitrogen and sulfur heteroatoms may optionally be oxidized, wherein the nitrogen heteroatom may optionally be quaternized, and including any bicyclic group in which any of the above heterocyclic rings is fused to a benzene ring.

Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, N-methylpiperazinyl, azetidinyl, N-methylazetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, tiazolyl and benzothienyl.

Heterocyclics can be unsubstituted or monosubstituted or disubstituted with substituents independently selected from hydroxy, halo, oxo (=O), alkylimino (RN= wherein R* is a loweralkyl group), amino, alkylamino, dialkylamino, alkoxy, thioalkoxy, polyalkoxy, loweralkyl, haloalkyl or cycloalkyl.

The most preferred heterocyclics include imidazolyl, pyridyl, piperazinyl, N-methylpiperazinyl, azetidinyl, N-methylazetidinyl, thiazolyl, thienyl, triazolyl and the following:

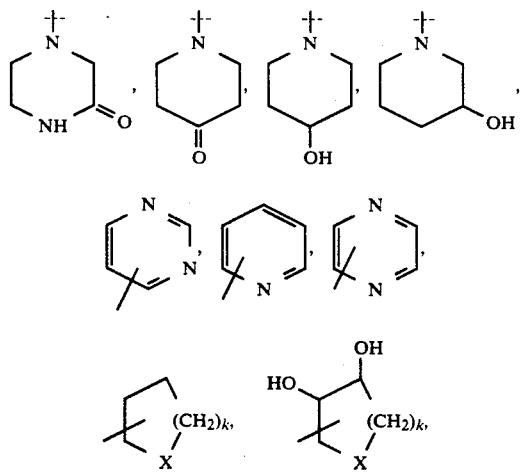

wherein k is 1 or 2 and X is N, NH, O, or S, provided that X is the point of connection only when X is N,

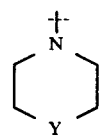

wherein Y is NH, N-loweralkyl, O, S, or SO$_2$, or

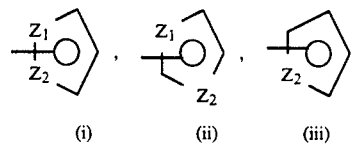

(i)  (ii)  (iii)

wherein the symbols (i), (ii) and (iii) represent 5-membered heterocycles containing one or more heteroatoms and containing 2 double bonds; wherein $Z_1$ is N, O, or S and not the point of connection and $Z_2$ is N when it is the point of connection and NH, O or S when it is not the point of connection; with the proviso that when $Z_2$ is the point of connection, then $Z_1$ is N.

The term "N-protecting group" or "N-protected" as used herein refers to those groups intended to protect the N-terminus of an amino acid or peptide or to protect an amino group against undesirable reactions during synthetic procedures or to prevent the attack of exopeptidases on the compounds or to increase the solubility of the compounds and includes but is not limited to sulfonyl, acyl, acetyl, pivaloyl, t-butyloxycarbonyl (Boc), carbonylbenzyloxy (Cbz), benzoyl or an L- or D-aminoacyl residue, which may itself be N-protected similarly.

The term "O-protecting group" as used herein refers to a substituent which protects hydroxyl groups against undesirable reactions during synthetic procedures and includes but is not limited to substituted methyl ethers, for example methoxymethyl, benzyloxymethyl, 2-methoxyethoxymethyl, 2-(trimethylsilyl)ethoxymethyl, benzyl and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "substituted amino" as used herein refers to:
 I) alkylamino,
 II) dialkylamino,
 III) (hydroxyalkyl)(alkyl)amino,
 IV) (dihydroxyalkyl)(alkyl)amino,
 V) alkoxycarbonylalkylamino,
 VI) carboxyalkylamino,
 VII) (amino)carboxyalkylamino,
 VIII) ((N-protected)amino)carboxyalkylamino,
 IX) (alkylamino)carboxyalkylamino,
 X) ((N-protected)alkylamino)carboxyalkylamino,
 XI) (dialkylamino)carboxyalkylamino,
 XII) (amino)alkoxycarbonylalkylamino,
 XIII) ((N-protected)amino)alkoxycarbonylalkylamino,
 XIV) (alkylamino)alkoxycarbonylalkylamino,
 XV) ((N-protected)alkylamino)alkoxycarbonylalkylamino,
 XVI) (dialkylamino)alkoxycarbonylalkylamino,
 XVII) (alkoxyalkyl)(alkyl)amino,
 XVIII) (alkoxyalkoxyalkyl)(alkyl)amino,
 XIX) di-(alkoxyalkyl)amino,
 XX) di-(alkoxyalkoxyalkyl)amino,
 XXI) di-(hydroxyalkyl)amino,
 XXII) ((unsubstituted heterocyclic)alkyl)(alkyl)amino,
 XXIII) ((substituted heterocyclic)alkyl)(alkyl)amino, XXIV) 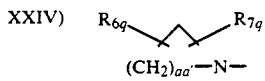

wherein aa' is 1 to 5 and $R_{6q}$ and $R_{7q}$ are independently selected from
1) hydrogen,
2) hydroxy,
3) alkoxy,
4) thioalkoxy,
5) alkoxyalkoxy,
6) carboxy,
7) alkoxycarbonyl,
8) halogen,
9) amino,
10) alkylamino,
11) dialkylamino,
12) alkylsulfonylamino,
13) arylsulfonylamino,
14) alkylaminocarbonylamino,
15) alkylaminocarbonyloxy,
16) alkoxycarbonyloxy, 17) 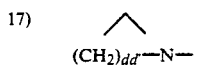

wherein dd' is 1 to 5, and
18) $R_{8q}$—$Z_q$— wherein $Z_q$ is O, S or NH and $R_{8q}$ is a $C_1$ to $C_6$ straight or branched carbon chain substituted by a substituent selected from hydroxy, alkoxy, thioalkoxy, alkoxyalkoxy, amino, alkylamino, dialkylamino, carboxy, alkoxycarbonyl, aryl and heterocyclic;

XXV) 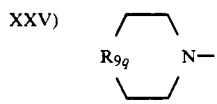

wherein $R_{9q}$ is
1) O,
2) S,
3) $SO_2$ or
4) C=O; or

XXVI) 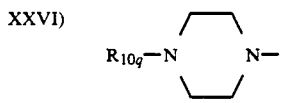

wherein $R_{10q}$ is
1) hydrogen,
2) loweralkyl,
3) an N-protecting group or
4) $R_{11q}$—C(O)— wherein $R_{11q}$ is aminoalkyl, (N-protected)aminoalkyl, 1-amino-2-phenylethyl or 1-(N-protected)amino-2-phenylethyl.

The term "substituted methylene group" as used herein refers to:
(I) —$CHR_{13q}R_{14q}$ wherein
1) $R_{13q}$ is
i) hydrogen or ii) hydroxy and
2) $R_{14q}$ is
i) hydrogen,
ii) loweralkyl, iii) hydroxy,
iv) hydroxyalkyl, v) alkoxy,
vi) alkoxyalkyl, vii) azido,
viii) azidoalkyl, ix) amino,
x) (N-protected)amino,
xi) aminoalkyl,
xii) (N-protected)aminoalkyl,
xiii) alkylamino,
xiv) (N-protected)(alkyl)amino, xv) alkylaminoalkyl,
xvi) (N-protected)(alkyl)-aminoalkyl,
xvii) dialkylamino,
xviii) dialkylaminoalkyl,
xix) carboxyalkyl, xx) thioalkoxy,
xxi) thioalkoxyalkyl,
xxii) alkylsulfonyl,
xxiii) alkylsulfonylalkyl,
xxiv) thioaryloxy,
xxv) thioaryloxyalkyl,
xxvi) arylsulfonyl,
xxvii) arylsulfonylalkyl,
xxviii) (unsubstituted heterocyclic)alkyl or
xxvix) (substituted heterocyclic)alkyl such that when $R_{13q}$ is hydroxy then
$R_{14q}$ is not hydroxy, alkoxy, azido, amino, alkylamino, dialkylamino, (N-protected)amino, (N-protected)(alkyl)amino, thioalkoxy, alkylsulfonyl or arylsulfonyl, and such that when $R_{13q}$ is hydrogen then $R_{14q}$ is not hydrogen or loweralkyl;
(II) —$C(=CH_2)C(O)NHR_{15q}$;
(III) —$C(OH)(R_{16q})C(O)NHR_{15q}$ or
(IV) —$CH(R_{16q})C(O)NHR_{15q}$ wherein
1) $R_{15q}$ is
i) loweralkyl,
ii) hydroxyalkyl,
iii) alkoxyalkyl, iv) aminoalkyl,
v) alkylaminoalkyl,
vi) dialkylaminoalkyl,
vii) aryl,
viii) heterocyclic or
ix) (heterocyclic)alkyl and
2) $R_{16q}$ is
i) hydrogen,
ii) loweralkyl,
iii) hydroxyalkyl, iv) haloalkyl or v) azidoalkyl;

(V) 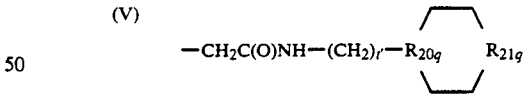

wherein
1) t' is 0 to 3,
2) $R_{20q}$ is
i) $CH_2$ or
ii) N and
3) $R_{21q}$ is
i) NH,
ii) O,
iii) S or
iv) $SO_2$,
such that when t' is 0 then $R_{20q}$ is $CH_2$ and when t' is 1 to 3 then $R_{20q}$ is N,
(VI) —$CH_2CH(R_{22q})C(O)NHR_{23q}$ wherein
1) $R_{22q}$ is
i) loweralkyl or ii) cycloalkylalkyl
and 2) $R_{23q}$ is
   i) loweralkyl,
   ii) hydroxyalkyl,
   iii) alkoxyalkyl, iv) aminoalkyl,
   v) alkylaminoalkyl,
   vi) dialkylaminoalkyl,
   vii) aryl,
   viii) arylalkyl
   ix) heterocyclic,
   x) (heterocyclic)alkyl or xi) 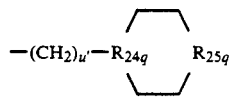

wherein
   a) u' is 0 to 3,
   b) $R_{24q}$ is $CH_2$ or N and
   c) $R_{25q}$ is NH, O, S or $SO_2$, such that when u' is 0 then $R_{24q}$ is $CH_2$ and when u' is 1 to 3 then $R_{24q}$ is N;

(VII) 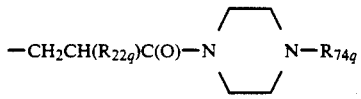

wherein
   1) $R_{22q}$ is as defined above and
   2) $R_{74q}$ is
      i) hydrogen,
      ii) loweralkyl,
      iii) an N-protecting group or
      iv) $R_{75q}$—C(O)—wherein $R_{75q}$ is aminoalkyl or (N-protected)aminoalkyl;

(VIII) 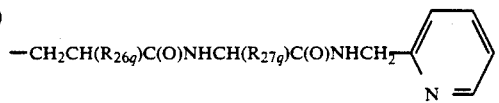

wherein
wherein
   1) $R_{26q}$ is
      i) loweralkyl or
      ii) cycloalkylalkyl and
   2) $R_{27q}$ is
      i) loweralkyl or
      ii) cycloalkylalkyl;
   (IX)  —$CH_2$  $CH(R_{81q})NHC(O)R_{82q}$  or —$CH_2CH(R_{81q})NHS(O)_2R_{82q}$ wherein
   1) $R_{81q}$ is
      i) loweralkyl or
      ii) cycloalkylalkyl and
   2) $R_{82q}$ is
      i) loweralkyl,
      ii) alkoxy,
      iii) alkylamino,
      iv) dialkylamino,
      v) —OR* wherein R* is aminoalkyl, alkylaminoalkyl, dialkylaminoalkyl or (heterocyclic)alkyl or vi) 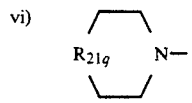

wherein $R_{21q}$ is as defined above;
   (X)  —$CH_2NHC(O)R_{82q}$ or —$CH_2NHS(O)_2R_{82q}$ wherein $R_{82q}$ is as defined above; or
   (XI)  —$CF_2CH(OH)R_{83q}$ wherein $R_{83q}$ is loweralkyl, loweralkenyl, cycloalkyl, cycloalkenyl, cycloalkylalkyl, cycloalkyenylalkyl, aryl, aryalkyl, heterocyclic or (heterocyclic)alkyl.

The terms "lipophilic or aromatic amino acid side chains" as used herein refer to amino acid side chains selected from the group isobutyl, isopropyl, sec-butyl, benzyl, p-methoxybenzyl, imidazole-4-yl-methyl, p-hydroxybenzyl, 1- and 2-naphthylmethyl, (pyrazolyl)methyl, (thiazolyl)methyl, cyclohexylmethyl, (3-indolyl)methyl, $CH_3SCH_2$— and the like. General references to amino acid side chains in both the description and claims herein is to be taken as reference to such, whether naturally occurring in proteins or not, and to both D- and L- forms.

The terms "Ala", "His", "Leu", "Phe", "Tyr", "Cys", "Gly", "Lys", "Sar", "Pro", "HomoPhe" and "norLeu" as used herein refer to alanine, histidine, leucine, phenylalanine, tyrosine, cysteine, glycine, lysine, sarcosine, proline, homophenylalanine and norleucine, respectively. In general, the amino acid abbreviations follow the IUPAC-IUB Joint Commission on Biochemical Nomenclature for amino acids and peptides (Eur. J. Biochem. 1984, 158, 9–31).

The chiral centers of the novel renin inhibiting compounds of the invention may have either the "R", "S" or "R,S" configuration. The terms "S" and "R" configuration are as defined by the IUPAC 1974 Recommendations for Section E, Fundamental Stereochemistry, Pure Appl. Chem. (1976) 45, 13–30.

Renin inhibitors having the general structure shown in group (9) can be prepared as described in Fung, et al., PCT Patent Application WO90/03971 (PCT/US89/04385), published Apr. 19, 1990, which is hereby incorporated by reference. The syntheses of segments containing substituents D are described in the Examples or have previously been described (Kempf, et al., J. Med. Chem. 1987, 30, 1978; Luly, et al., J. Med. Chem. 1987, 30, 1609; Buhlmayer, et al., U.S. Pat. No. 4,727,060; Morisawa, et al., European patent application No. 0228192; Ten Brink, PCT Patent Application No. WO87/02986).

Renin inhibitors having the general structure shown in group (10) can be prepared as described in De, et al., PCT Patent Application No. WO90/04917 (PCT/US89/04649), published May 17, 1990, which is hereby incorporated by reference. The syntheses of segments containing substituents $R_5$ are described in the Examples or have previously been described (Kempf, et al., J. Med. Chem. 1987, 30, 1978; Luly, et al., J. Med. Chem. 1987, 30, 1609; Buhlmayer, et al., U.S. Pat. No. 4,727,060; Morisawa, et al., European patent application No. 0228192; Ten Brink, PCT Patent Application No. WO87/02986).

The following examples will serve to further illustrate preparation of the novel compounds of the invention.

EXAMPLE 1

2(S)-(1(S)-(4-(Methoxymethoxy)piperidin-1-yl)carbonyl-2-phenyl)ethoxyhexanoic acid amide of 3-(4-morpholinyl)propyl-5(S)-amino-6-cyclohexyl-4(S)-hydroxy-2(S)-isopropylhexanamide

Example 1A:
4(S)-t-Butyloxycarbonylamino-5-cyclohexyl-3(R,S)-hydroxy-1-pentene To a stirred −78° C. solution of Boc-cyclohexylalanine methyl ester (10.2 g, 35.8 mmol) in dry toluene (60 ml) was added diisobutylaluminum hydride (34 ml of a 1.5M solution in toluene). After 30 min, vinyl magnesium bromide (108 ml of 1M solution in tetrahydrofuran (THF)) was added. After stirring for 15 h at 0° C., the mixture was carefully quenched with methanol, treated with Rochelle salts (22 ml of saturated aqueous solution in 140 ml $H_2O$), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g of the desired product. Anal. calcd. for $C_{16}H_{29}NO_3 \cdot \frac{1}{4} H_2O$: C, 66.8; H, 10.3; N, 4.9. Found: C, 66.9; H, 10.2; N, 4.7.

Example 1B:
3-(t-Butyloxytcarbonyl)-4-(cyclohexylmethyl)-2,2-dimethyl-5-vinyloxazolidine.

The procedure of S. Thaisrivong (J. Med. Chem. 1987, 30, 976) was employed. A solution of 40 g of the resultant compound of Example 1A and 102 g of 2-methoxypropene in 250 ml of dichloromethane was stirred at room temperature. Solid pyridinium p-toluenesulfonate (PPTS) (177 g) was added slowly to the reaction mixture. After addition was complete, the reaction was stirred for 1 h and neutralized by addition of solid sodium bicarbonate. The solids were filtered and the filtrate was concentrated. Flash chromatography on silica gel gave 57 g of the desired compound. IR($CDCl_3$) 1690 (C=O carbamate)$cm^{-1}$; $^1$HNMR ($CDCl_3$) 5.95 (m,1H), 5.32 (m,1H), 5.20 (dt,1H), 4.27 (dd,1H), 1.47 (s,9H).

Anal. Calcd. for $C_{19}H_{33}NO_3$ C, 70.55; H, 10.28; N, 4.33.
Found: C, 70.47; H, 10.27; N, 4.09.

Example 1C:
3-(t-Butyloxycarbonyl)-4-(cyclohexylmethyl)2,2-dimethyloxazolidine-5-carboxaldehyde.

A solution of 10 g of the resultant compound of Example 1B in 150 ml of 2:1 dichloromethane:methanol was cooled in an dry-ice acetone bath. Ozone was bubbled through the solution until a blue color persisted (1 h). Dry nitrogen was then bubbled through the reaction mixture to remove excess dissolved ozone. The reaction mixture was cannulated into a suspension of 8 g zinc dust, 8 ml glacial acetic acid, 200 ml water, and 200 ml of methanol cooled to −45° C. After 5 min the bath was removed and the mixture allowed to warm to room temperature overnight. 100 ml of saturated sodium chloride was added and the entire reaction mixture extracted with two 300 ml portions of dichloromethane. The combined dichloromethane extracts were decanted, dried (MgSO₄), filtered, and evaporated. The crude aldehyde was purified by flash chromatography (1:4) ethyl acetate:hexane to give 9.7 g of the desired compound as a mixture of diastereomers (3:1 trans:cis) as judged by the integrated resonances of the two aldehyde protons. IR($CDCl_3$) 1735 (C=O aldehyde), 1690 (C=O carbamate)$cm^{-1}$; $^1$HNMR ($CDCl_3$ 9.83 (s,1H,CHO), 9.73 (d,1H,CHO cis diastereomer), 4.14 (m,1H), 1.46 (s,9H).

Anal. Calcd. for $C_{18}H_{31}NO_4$ C, 66.43; H, 9.60; N, 4.30. Found: C, 65.27; H, 9.79; N, 4.20.

Equilibration of Aldehyde Isomers

A suspension of 25 g of the above aldehyde in 300 ml of methanol and powdered potassium carbonate (10.7 g) was stirred at room temperature for 6 h. The reaction mixture was cooled in an ice-water bath and treated with 9.3 g of glacial acetic acid for 5 min. A solution of 0.5M sodium dihydrogen phosphate (300 ml) was added to the mixture. After 30 min, the solution was concentrated to one-half the volume under reduced pressure and extracted with ether (600 ml). The combined ether extracts were dried (MgSO₄), filtered, and concentrated. The aldehyde was purified by flash chromatography using (1:4) ethyl acetate:hexane to give 19.5 g of the desired compound as an 8:1 mixture of trans:cis diastereomers.

Example 1D: 3-(3(R)-(3-(tert-Butyloxycarbonyl)-2,2 dimethyl-4(S)-cyclohexylmethyl-5(R)-oxazolidinyl)-3-hydroxy-2(R)isopropyl1-oxopropyl)-4(R)-methyl-5(S)-phenyl-2-oxazolidinone.

The title compound was prepared in analogy to the procedure of S. Thaisrivongs, D. T. Pals, L. T. Kroll, S. R. Turner and F. S. Han, J. Med. Chem. 1987, 30, 976–82, from the resultant compound of Example 1C, in 63% yield. M. p. 97° C. $^1$HNMR ($CDCl_3$) 0.91 (d, 3H), 1.06 (d, 3H), 1.1 (d, 3H), 1.48 (s, 9H), 0.9–1.9 (several bm, 12H total), 2.12 (bd, 1H), 2.3 (m, 1H), 3.81 (dd, 1H), 3.94 (td, 1H), 4.04 (bm, 1H), 4.22 (dd, 1H), 4.84 (dq, 1H), 5.61 (d, 1H), 7.31–7.45 (m, 5H). High resolution mass spectrum. Calcd. for (M+H)+ Of $C_{33}H_{51}N_2O_7$: 587.3698. Found: 587.3696.

Analysis. Calcd. for $C_{33}H_{50}N_2O_7$: C, 67.55; H, 8.59; N, 4.77. Found: C, 67.41; H, 8.61; N, 4.77.

Example 1E:
3-(3(R)-(3-(tert-Butyloxycarbonyl)-2,2-dimethyl-4(S)cyclohexylmethyl-5(R)-oxazolidinyl)-3-((1-imidazolyl)thionyloxy)-2(R)-isopropyl-1-oxopropyl)-4(R)-methyl-5(S)-phenyl-2-oxazolidinone.

The resultant compound from Example 1D (1.840 g, 3.136 mmol) and 1,1′-thiocarbonyldiimidazolide (1.128 g, 6.330 mmol) were refluxed in 8 mL dry 1,2-dichloroethane under a nitrogen atmosphere for 24 h. The mixture was concentrated and the residue purified by flash chromatography (2.5% MeOH—$CH_2Cl_2$) to afford 1.896 g (87%) of the title compound. $^1$H NMR($CDCl_3$) 0.93 (d, 3H), 1.04 (d, 3H), 1.08 (d, 3H), 1.5 (bs, 9H), 0.9–1.9 (several bm, 13H total), 2.05 (m, 1H), 4.13 (bm, 1H), 4.23 (dd, 1H), 4.81 (dd, 1H), 4.94 (dq, 1H), 5.70 (d, 1H), 6.33 (dd, 1H), 7.06 (bs, 1H), 7.3–7.5 (m, 5H), 7.61 (bs, 1H), 8.40 (bs, 1H). High resolution mass spectrum. Calcd. for (M+H)+ of $C_{37}H_{53}N_4O_7S$: 697.3635. Found: 697.3629. Analysis. Calcd. for $C_{37}H_{52}N_4O_7S$: C, 63.77; H, 7.52; N, 8.04. Found: C, 63.58; H, 7.44; N, 7.94.

EXAMPLE 1F: 3-(3-(3-(tertButyloxycarbonyl) 2,2-dimethyl-4(S)-cyclohexylmethyl-5(S)-oxazolidinyl)-2(R)-isopropyl-1-oxopropyl)-4(R)-methyl-5(S)-phenyl-2-oxazolidinone.

A solution of the resultant product from Example 1E (6.50 g, 9.33 mmol) in 275 ml of dry toluene was degassed with argon for 30 min, then warmed to reflux (under argon). A solution of tri-n-butyltin hydride (5.43 g, 18.6 mmol) in 75 ml of dry, degassed toluene was added dropwise over 15 min. After an additional 2 h of reflux, the reaction was cooled, concentrated and purified by flash chromatography (5% EtOAc-hexanes) to afford 4.82 g (90%) of the title compound as a white foam. $^1$H NMR(CDCl$_3$) 0.90 (d, 3H), 0.92 (d, 3H), 0.9-1.1 (bm, 3H), 1.06 (d, 3H), 1.15-1.35 (bm, 3H), 1.51 (s, 9H), 1.57-2.14 (several bm, 16H total), 3.84 (m, 1H), 3.97 (m, 1H), 4.85 (dq, 1H), 5.68 (d, 1H), 7.3-7.46 (m, 5H). Mass spectrum: (M+H)+ =571.

Analysis. Calcd. for C$_{33}$H$_{50}$N$_2$O$_6$: C, 69.44; H, 8.83; N, 4.91. Found: C, 69.31; H, 8.82; N, 4.89.

EXAMPLE 1G:
2(S)-((3-(tert-Butyloxycarbonyl-2,2-dimethyl-4(S)-cyclohexylmethyl-5(S)-oxazolidinyl)methyl)-3-methylbutanoic acid.

Using the procedure of D. A. Evans, T. C. Britton and J. A. Ellman, Tetrahedron Lett. 1987, 28(49), 6141-44, the resultant product from Example 1F (6.10 g, 10.7 mmol) was hydrolyzed with aq. LiOH and hydrogen peroxide in THF. The crude material was purified by flash chromatography (15% EtOAc-0.5% HOAc-hexanes) to provide 3.53 g (90%) of the title compound as a viscous colorless oil. $^1$H NMR(CDCl$_3$) 0.96 (d, 3H), 1.00 (d, 3H), 1.1-1.3 (bm, 5H), 1.48 (s, 9H), 1.5-1.9 (several bm, 15H total), 2.0 (m, 1H), 2.66 (m, 1H), 3.7 (bm, 1H), 3.90 (m, 1H). Mass spectrum: (M+H)+ =412.

Analysis. Calcd. for C$_{23}$H$_{41}$NO$_5$.0.25 H$_2$O: C, 66.39; H, 10.05; N, 3.37. Found: C, 66.46; H, 9.84; N, 3.36.

EXAMPLE 1H: 3-(4-Morpholinyl)propyl 2(S)-((3-tert-butyloxycarbonyl)-2,2-dimethyl-4(S)-cyclohexylmethyl-5(S)-oxazolidinyl)methyl-3-methylbutanamide.

The procedure of P. Buhlmayer, et. al., J. Med. Chem. 1988, 31(9), 1839-46 was adapted. The resultant compound from Example 1G (75 mg, 0.182 mmol), HOBT (42.0 mg, 0.274 mmol) and N-methylmorpholine (55 mg, 0.55 mmol) were dissolved in 1.0 ml dry DMF, and the solution was cooled to −20° C. (under nitrogen). EDAC (53 mg, 0.28 mmol) was added as a solid, and the resulting mixture was stirred at −20° to 0° C. for 1 h. The mixture was sealed, and allowed to react at 0° C. (in refrigerator) for 48 h. To the resulting solution was added 4-(3-aminopropyl)morpholine (0.23 mmol). The resulting solution was stirred at 0° C. for 4 h, and for a further 20 h, allowing it to warm slowly to room temperature. The volatiles were removed by high vacuum distillation, and the residue was partitioned between CH$_2$Cl$_2$ and aq. NaHCO$_3$. The aqueous phase was extracted 3× with CH$_2$Cl$_2$, and the combined organic phases were washed with brine, dried (Na$_2$SO$_4$) and concentrated. Purification by flash chromatography (4% MeOH—CH$_2$Cl$_2$) provided the desired compound.

$^1$H NMR(CDCl$_3$) 0.92 (d, 3H), 0.95 (d, 3H), 1.46 (s) and 1.48 (s, 12H total), 1.57 (bs, 3H), 0.8-1.8 (several bm, 18H total), 2.01 (m, 1H), 2.46 (bm, 6H), 3.37 (m, 2H), 3.64 (bm, 1H), 3.75 (bm, 5H), 6.80 (bt, 1H). High resolution mass spectrum. Calcd. for (M+H)+ of C$_{30}$H$_{56}$N$_3$O$_5$: 538.4220. Found: 538.4220.

EXAMPLE 1I:
1(S)-(4-(Methoxymethoxy)peperidin-1-yl-carbonyl)-2-phenylethanol.

A solution of 176 g (1.3 mol) of 1hydroxybenzotriazole (Aldrich), 80 g (0.48 mol) of L-3-phenyllactic acid (prepared from L-phenylalanine), 76 g (0.52 mol) of 4-(methoxymethoxy)piperidine in 800 mL of DMF was cooled to −25° C. (internal temperature) while 132 g EDC HCl (Saber Labs) was added (mechanical stirring). After addition, the reaction was stirred to rt over 24 h. Excess DMF was removed under high vacuum and the residue dissolved into 1.5L of ethyl acetate. The ethyl acetate solution was washed with 4L of saturated sodium bicarbonate. The ethyl acetate layer was separated, dried (MgSO$_4$) and evaporated to give approximately 138 g of crude amide. The product was isolated by silica gel chromatography using ethyl acetate/hexane as eluant. Yield 120 g (79%).

$^1$H NMR(CDCl$_3$, TMS) 1.61 (m,2H), 1.81 (m,2H), 2.89 (m,2H), 3.38 (s,3H), 3.5 (m,2H), 3.79 (m,2H), 3.96 (m,1H), 4.62 (t, 1H), 4.68 (s, 2H).

EXAMPLE 1J:
2(S)-(1(S)-(4-(Methoxymethoxy)piperidin-1-yl-carbonyl)-2-phenylethoxy)hexanoic acid.

The resultant compound of Example 1I (1.45 g, 4.95 mmol), in 10 ml THF was added dropwise to the cooled suspension of sodium hydride (60% dispersion in oil, 0.5 g, 11.2 mmol) in 4 ml THF (0°-5° C.). The suspension was stirred for 20 mins at 0°-5° C. and then warmed up to room temperature and stirred for additional 1 h. Solution of D-2-bromohexanoic acid in 6 ml THF was added dropwise to the cooled suspension (0°-5° C.) under N$_2$ atmosphere. It was then allowed to warm up to room temperature and stirred overnight, quenched with cold H$_2$O and extracted with ethylacetate to remove undesired starting material. It was acidified with 1M sodium hydrogen sulfate and extracted with chloroform. After filtration and evaporation, the crude product was purified on silica gel, eluted with CH$_2$Cl$_2$: CH$_3$OH:A$_c$OH (19.4:0.3:0.3) to obtain 0.79 g of desired acid (43% yield).

$^1$H NMR(CDCl$_3$, TMS) 0.88 (t,3H), 3.35 (s,3H), 3.98 (bt,1H), 4.6 (m,1H), 4.64 (s,2H), 7.38 (m,5H). Mass spectrum: (M+H)+ =408.

EXAMPLE 1K:
2(S)-(1(S)-(4-(Methoxymethoxy)piperidin-1-ylcarbonyl-2-phenyl)ethoxyhexanoic acid amide of 3-(4-morpholinyl)propyl 5(S)-amino-6-cyclohexyl-4(S)-hydroxy-2(S)-isopropylhexanamide.

The resultant compound from Example 1H (0.161 mmol) was deprotected by dissolving in 1.0 ml dry CH$_2$Cl$_2$, cooling the solution to −10° C. (under nitrogen), and treating with 1.0 ml of trifluoroacetic acid. The resulting solution was stirred at −10° to 0° C. for 4 h. The solvents were largely removed with a stream of nitrogen, and the residue (as a concentrated solution in trifluoroacetic acid) was dissolved in 1.0 ml THF and 0.3 ml water at 0° C. The solution was allowed to warm slowly to ambient temperature over 18 h. The crude aminoalcohol was isolated by basifying the reaction with an excess of 1.0M aq. Na$_2$CO$_3$, saturating the solution with NaCl, and extracting with 5×10 ml of 5% EtOH—CHCl$_3$. The combined organic phases were washed with brine, dried (Na$_2$SO$_4$), concentrated, and the residue placed under high vacuum overnight to yield 66.2 mg (100%) of yellow viscous oil.

Coupling was achieved by combining the resultant compound from Example 1J (72 mg, 0.177 mmol), the above aminoalcohol (0.168 mmol), HOBT (34 mg, 0.22 mmol) and N-methylmorpholine (25 mg, 0.25 mmol) in 1.0 ml dry DMF. The resulting solution was cooled to −20° C. (under argon), and EDAC (45 mg, 0.23 mmol) was added. The reaction was allowed to slowly warm to room temperature as the ice bath melted, for a total of 24 h. The solvent was removed by high vacuum distillation, and the residue was partitioned between 15 ml CH$_2$Cl$_2$, 9 ml sat. aq. NaHCO$_3$ and 1 ml H$_2$O. The aqueous phase was further extracted (3×10 ml CH$_2$Cl$_2$), and the combined organic phases were washed with 10 ml brine, dried (Na$_2$SO$_4$) and concentrated. Purification by flash chromatography yielded the title compound as a hygroscopic glassy solid, m.p. 49°–51° C. $^1$H NMR(CDCl$_3$) 0.90 (m), 0.91 (d) and 0.92 (d, 9H total), 0.65–1.90 (several bm, approx. 28H total), 2.02 (m, 1H), 2.45 (bm, 6H), 2.95 (m, 1H), 3.05 (dd, 1H), 3.20 (bm, 2H), 3.36 (s, 3H), 3.45 (m, 2H), 3.6–4.0 (several bm) and 3.71 (m, 10H total), 4.48 (dd, 1H), 4.68 (s, 2H), 5.80 (d) and 5.88 (d, 1H total), 6.87 (bt, 1H), 7.3 (bm, 5H). Mass spectrum: (M+H)+ =787.

EXAMPLE 2

2(S)-(1(S)-(4-Methoxymethoxy)piperidin-1-yl)carbonyl-2-phenyl)ethoxyhexanoic acid amide of 3-(4-morpholinyl)propyl-5(S)-amino-6-cyclohexyl-4(S)-hydroxy-2(S)-isopropylhexanamide (Alternate Preparation)

EXAMPLE 2A

2(S)-Cyclohexylalanine methyl ester, hydrochloride salt

L-Phenylalanine (215 g, 1.3 mole) was hydrogenated over Pd/C in HOAc, filtered and concentrated. The resulting cyclohexylalanine was taken up in MeOH (1200 mL). Thionyl chloride (427 g, 3.59 mole) was slowly added to the slurry, which eventually became homogeneous. The reaction was cooled in an ice/water bath and addition of thionyl chloride was continued. The reaction mixture was heated to reflux for 2 h, cooled and concentrated to afford a solid, which was taken up in ether and filtered. The white solid was washed with ether in the filter funnel and dried in vacuo to give 271 g of product, 94% yield over two steps.

EXAMPLE 2B

2(S)-N-(Triphenylmethyl)cyclohexylalanine methyl ester

Cyclohexylalanine methyl ester, HCl salt (88 g, 398 mmol) was taken up in chloroform (400 ML). Triethylamine (84.6 g, 836 mmol) was then added in one portion to the slurry and stirred five minutes. Triphenylmethylchloride (111 g, 398 mmol) was then added, and the reaction was stirred for 5 h at ambient temperature. The internal temperature of the reaction reached 50° C., however, external cooling was not employed. The reaction mixture was washed with 1M KHSO$_4$ solution (2×100 mL), saturated NaHCO$_3$ (200 mL), brine (100 mL), then dried over MgSO$_4$. The solution was then concentrated to give 200 g of residue which was filtered through 900–1000 g of silica gel (elution gradient hexane-10:1 hexane: ethyl acetate) affording 157 g of product (93%), which could be crystallized from hexanes: ethyl acetate to afford large white crystals.

EXAMPLE 2C

Dimethyl 3(S)-4-Cyclohexyl-(N-triphenylmethyl)amino-2-oxobutylphosphonate

To a −78° C. solution of dimethyl methylphosphonate (272.5 g, 2.2 mol) in 1.6L THF was added n-BuLi (2.5M, 800 mL, 2.0 mmol) and stirred 45 minutes. The product of Example 2B (156 g, 366 mmol) in 40 mL THF was then added dropwise. This reaction mixture was stirred at −50° C. for 3 h, then at −40° C. for 6 h then finally warmed to ambient temperature overnight. The reaction mixture was concentrated, taken up in ether, washed with 1M KHSO$_4$, saturated NaHCO$_3$ (twice) and brine, dried and concentrated. The residue (200 g) was filtered through 1000 g silica gel, (1:1 hexanes: ethyl acetate) to give 135 g of beta-keto phosphonate (72%) as an oil.

EXAMPLE 2D

6(S)-7-Cyclohexyl-2-methyl-6-(N-triphenylmethyl)-amino-5-oxohept-2-ene-3-oic acid The product of Example 2C (117.2 g, 229 mol) was dissolved in 600 ml THF and cooled to 0° C. To this solution was added hexanes washed NaH (60%, 9.6 g(wet), 240 mmol) and the mixture was stirred 30 min. Next was added methyl 3-methyl-2-oxobutyrate (29.8 g, 229 mmol) in 100 ml THF and stirred at 0° C. for 4 h. Volatiles were removed at reduced pressure, the residue was disolved in 1:1 hexanes: ether (500 ml) and washed with water (100 ml), NaHCO$_3$ (200 ml), brine (200 ml), dried (MgSO$_4$) and concentrated to afford 129 g of the desired ester as an oil. This material (123 g) was taken up in 460 ml THF, 229 ml MeOH, cooled to 0° C. then 18.86 g of LiOH-H$_2$O in 229 ml of distilled water was added. This solution was allowed to warm to room temperature and stirred for 3 days. Volatiles were removed at reduced pressure and the resulting aqueous solution was washed with ether (100 ml×2) then acidified to pH 3 with 6N HCl. The aqueous solution was then extracted with EtOAc (300 ml×2), washed with brine, dried (MgSO$_4$) and concentrated to give 116 g of a yellow foam. This material was recrystallized from 525 ml of hot hexanes/EtOAc (12/1) to give 72.4 g of a white solid (62% for three steps).

EXAMPLE 2E

N-Hydroxysuccinimide ester of 6(S)-7-Cyclohexyl-2-methyl-6-(N-triphenylmethyl)-amino-5-oxohept-2-ene-3-oic acid A solution of 3.06 g (6.0 mmol) of the product of Example 2D in 50 ml THF was added to 6.8 g (60 mmol) of N-hydroxysuccinimide. This homogeneous solution was cooled to 0° C., then DCC (1.25 g, 12 mmol) in 5 ml THF was added. The cooling bath was removed and the reaction was stirred for 2 h. At this time, an additional 1.25 g of DCC was added. After 5 h of total reaction time, the mixture was filtered, concentrated and dissolved in either. The organics were washed with NaHCO$_3$ (aq, 50 ml×2), brine, dried (MgSO$_4$) and concentrated at reduced pressure to give 5.2 g of product as an oil, which was dissolved in 20 ml ether. A 1N solution of HCl/Ether (30 ml) was added. A gummy solid immediately precipitated out of solution; CH$_2$Cl$_2$ (25 ml) was added and the clear reaction mixture was stirred overnight. After 12 h, the product which precipitated from the mixture was collected by filtration and washed with ether to give, after drying, 2.1 g of a white solid in 87% yield for two steps.

EXAMPLE 2F (5S,6S)-6-Cyclohexylmethyl-3-isopropylidene-5-hydroxypiperidine-2-one To a 0° C. slurry of the product of Example 2E (1.2 g, 3.0 mmol) in 20 ml CH$_2$Cl$_2$ was added imidazole (204 mg, 3.0 mmol). The resulting reaction mixture was stirred for 1 h, then washed with 20 ml of KHSO$_4$, water, saturated NaHCO$_3$, and brine. The organic portion was dried over MgSO$_4$, filtered and cooled to −78° C. To the cold solution was added L-Selectride ® (Aldrich, 1.0M, 5.0 ml, 5.0 mmol) and stirred for 10 min. The reaction mixture was then warmed to −40° C. and quenched with 20% citric acid solution. The organics were washed with 20 ml of water, saturated NaHCO$_3$ solution, brine, dried over MgSO$_4$, and concentrated to afford a clear oil. This residue was purified on silica gel (50% hexanes/ethyl acetate) to give an oil which was triturated with ether to afford a white solid, 545 mg, 72% yield from active ester.

EXAMPLE 2G (2S,4S,5S)-6-Cyclohexylmethyl-2-isopropyl-5-amino-4-hexanolide

A solution of the product of Example 2F (24.7 g, 98.4 mmol) in 500 ml of ethyl acetate was treated with 2.5 g of dry Pd/C and hydrogenated at 4 atm for 4 h at ambient temperature. The reaction mixture was filtered and concentrated to a white foamy solid which was taken on without further purification.

The saturated lactam was dissolved in 200 ml of 6N HCl and 50 ml of ethanol then heated to reflux for 14 h. The reaction mixture was concentrated at reduced pressure and azeotropically dried with toluene to afford a pale oil. This material was taken up in water and extracted with hexane, then made basic by addition of a solution of NaHCO$_3$. Extraction with ethyl acetate followed by drying (MgSO$_4$) and removal of volatiles afforded a yellowish oil which solidified to a white solid upon standing. Recrystallization from hexane gave 20.7 g (90%) of product as white needles.

EXAMPLE 2H

2(S)-(1(S)-(4-Methoxymethoxy)piperidin-1-yl)carbonyl-2-phenyl)ethoxyhexanoic acid amide of 3-(4-morpholinyl)propyl-5(S)-amino-6-cyclohexyl-4(S)-hydroxy-2(S)isopropylhexanamide The product of Example 2G is reacted with 4-(3-aminopropyl)morpholine and the resulting product is coupled with the product of Example 1J according to the procedure of Example 1K to provide the desired compound.

EXAMPLE 3

(2S)-2-Benzyl-3-(1-methylpiperazin-4-ylsulfonyl)propionyl-(L)-(4-Thiazolyl)Ala Amide of (2S,3R,4S)-2-Amino-1-cyclohexyl-3,4-dihydroxy-6-methylheptane

EXAMPLE 3A

Methyl 3-Hydroxy-2-methylene-3-phenylpropionate

A mixture of benzaldehyde (82.1 mL, 0.81 mol), methyl acrylate (109.1 mL, 1.211 mol), 1,4-diazabicyclo(2,2,2)octane (13.6 g, 0.12 mol), and acetic acid (1.4 mL, 0.024 mol) was allowed to stir at 35° C. for 60 h, at which point the reaction was determined to have proceeded to 70% completion by $^1$H NMR. Methyl acrylate (20.9 mL, 0.23 mol) was then added and the solution was allowed to react at 35° C. for an additional 48 h. The mixture was diluted with diethyl ether (1.0 L) and was washed with 2×200 mL portions of a pH 7 phosphate buffer. After concentration in vacuo, the remaining mixture was distilled at reduced pressure (12 mm) to afford 6.5 g of unreacted benzaldehyde and 130.0 g (90%) of the desired product as a colorless oil: b.p. 130° C. (12 mm); IR (film) 1718, 1440 cm$^{-1}$; $^1$H NMR (CDCl$_3$) delta 3.67 (s, 3H), 5.52 (br s, 1H), 5.83–5.85 (m, 1H), 6.29–6.31 (m, 1H), 7.23–7.39 (m,5H); $^{13}$C NMR (75 MHz, CDCl$_3$) delta 51.8, 72.9, 125.8, 126.5, 127.7, 128.3, 141.2, 141.9, 166.6.

EXAMPLE 3B (Z)-1-Bromo-2-carbomethoxy-3-phenyl-2-propene

To a 2L, 3-neck Morton flask fitted with a thermometer, a mechanical stirrer, and an addition funnel was added the resultant compound from Example 3A (305.9 g, 1.585 mol) followed by addition of 48% HBr (505 mL, 4.46 mol) in one portion. The flask was immersed in an ice-water bath, at which time concentrated sulfuric acid (460 mL, 8.62 mol) was added dropwise over 90 min and the internal temperature of the reaction mixture was maintained at 23°–27° C. throughout the addition process. After removal of the ice-water bath, the mixture was allowed to stir at ambient temperature overnight. The solution was then transferred to a separatory funnel and the organic layer was allowed to separate from the acid layer. The acids were drained and the organic layer was diluted with 2L of a 1:1 ethyl acetate/hexane solution, washed with saturated aqueous sodium bicarbonate solution (1L), dried over sodium sulfate, and concentrated to yield 400 g (99%) of the desired product as a light yellow oil, which was used without any additional purification: b.p. 180° C. (12 mm); IR (film) 1718, 712 cm$^{-1}$; $^1$H NMR (CDCl$_3$) delta 3.89 (s, 3H), 4.40 (s, 2H), 7.38–7.45 (M, 3H), 7.56–7.60 (m, 2H), 7.83 (s, 1H); $^{13}$C NMR (75 MHz, CDCl$_3$) delta 26.77, 52.47, 128.63, 128.87, 129.61, 134.20, 142.95, 166.62.

EXAMPLE 3C (Z)-2-Carbomethoxy-3-phenyl-2-propene-1-sulfonic Acid Sodium Salt To a 12L, 3-neck round bottom flask fitted with a mechanical stirrer, thermometer and an addition funnel was added the resultant product from Example 3B (400 g, 1.57 mol) and methanol (4L). The mixture was warmed to 50° C. and a solution of sodium sulfite (199 g, 1.57 mol) dissolved in water (4L) was added over 75 min while the internal temperature of the flask was maintained at 50° C. After the addition was complete, the clear solution was allowed to stir at 50° C. for an additional 45 min. The reaction mixture in solution was taken to the next step without additional purification. The compound can be isolated by concentration to an amorphous powder, which is contaminated with an equivalent of sodium bromide: IR (KBr) 1711, 1628, 1215 cm$^{-1}$; $^1$H NMR (DMSO D-6) delta 3.70 (s, 3H), 3.77 (s, 2H), 7.33–7.41 (m, 3H), 7.48 (s, 1H), 7.87–7.89 (m, 2H); $^{13}$C NMR (75 MHz, DMSO D-6) delta 49.88, 51.93, 127.36, 128.33, 128.91, 129.82, 134.75, 139.06, 168.60.

EXAMPLE 3D

2-Carbomethoxy-3-phenylpropane-1-sulfonic Acid Sodium

To the 8L of 1:1 methanol/water mixture containing the resultant compound from Example 3C was added 60 g of W-24 raney nickel. The resulting suspension was pressurized under 50 psi of hydrogen and was allowed to shake on a Parr shaker for 24 h, at which time an additional 20 g of raney nickel catalyst was added. After 6 h under 50 psi of hydrogen, the catalyst was removed by filtration and the solution was concentrated to dryness. To the dry white solid was added ethyl acetate (6L) and heptane (4L) and the solution was vigorously stirred with a mechanical stirrer overnight. The white suspension was removed by filtration yielding 530 g (88%) of the desired product as an amorphous powder that was contaminated with approximately one equivalent of NaBr. The compound was used without any additional purification: IR (KBr) 1740, 1215, 1050 cm$^{-1}$. $^1$H NMR (DMSO D-6) delta 2.48–2.54 (m, 1H), 2.74–2.87 (m, 2H), 2.91–3.04 (m, 2H), 3.48 (s, 3H), 7.12–7.32 (m, 5H); $^{13}$C NMR (75 MHz, D$_2$O/DMSO D-6) delta 38.18, 44.80, 52.67, 52.82, 127.42, 129.13, 129.34, 138.14, 176.84.

EXAMPLE 3E

2-Carbomethoxy-3-phenyl-1-propanesulfonyl Chloride

To a 3L round bottom flask was added the resultant compound from example 3D (530 g, 1.39 mol) and toluene (520 mL) followed by the addition of PCl$_5$ (317 g, 1.52 mol). The mixture was warmed to 50° C. with stirring for 45 min. It was then diluted with toluene (1L) and was filtered through celite. After concentration in vacuo, 371 g (96%) of the desired product was obtained as a light brown oil: IR (film); 1740, 1380, 1170 cm$^{-1}$; $^1$H NMR (CDCl$_3$); delta 2.92 (dd, 1H, J=8.1, 14.0), 3.17 (d, 1H, J=6.6, 14.0), 3.41-3.50 (m, 1H), 3.67 (dd, 1H, J=3.3, 14.3), 3.72 (s, 3H), 4.20 (dd, 1H, J=8.8, 14.3), 7.15–7.18 (m, 2H), 7.25–7.35 (m, 3H); $^{13}$C NMR (75 MHz, CDCl$_3$) delta 37.26, 42.88, 52.65, 64.89, 127.49, 128.87, 128.92, 135.61, 171.79.

EXAMPLE 3F

Methyl 2-Benzyl-3-(1-methyl-piperazin-4-ylsulfonyl)propionate

To a 1L round bottom flask was added the resultant compound from Example 3E (84.5 g, 0.305 mol) and dichloromethane (305 mL). The mixture was cooled to 0° C. in an ice water bath and a solution of N-methyl piperazine (35.5 mL, 32.1 g) dissolved in dichloromethane (305 mL) was added dropwise with vigorous stirring over 90 min. After the addition was completed, the ice-water bath was removed and the mixture was stirred an additional 4 h while warming to ambient temperature. The solution was then poured into a separatory funnel containing 1L of a 5% aqueous NaOH solution. The layers were partitioned and the organic layer was dried over potassium carbonate. Concentration in vacuo yielded an oil, which was filtered through 200 g of silica gel using 4:1 hexane/ethyl acetate as an eluant. Concentration gave 84.3 g (81%) of the desired product as a yellow oil: IR (film); 1735, 1165, 955 cm$^{-1}$; $^1$H NMR (CDCl$_3$) delta 2.30 (s, 3H), 2.42 (t, 4H, J=4.8), 2.88 (dd, 1H, J=7.7, 14.0), 2.93 (dd, 1H, J=3.7, 14.0), 3.06 (dd, 1H, J=7.0, 13.6), 3.18–3.27 (m, 5H), 3.43 (dd, 1H, J=8.82, 13.9), 3.67 (s, 3H), 7.14–7.17 (m, 2H), 7.24–7.34 (m, 3H); $^{13}$C NMR (75 MHz, CDCl$_3$) delta 37.91, 42.22, 45.36, 45.83, 49.61, 52.21, 54.36, 127.06, 128.66, 128.92, 129.06, 136.79, 173.33.

EXAMPLE 3G (2S) 2-Benzyl-3-(1-methyl-piperazin-4-ylsulfonyl)propionic Acid

The resultant racemic ester from Example 3F (135 g, 397 mmol) was suspended in acetone (300 mL) and water (900 mL). While being stirred vigorously at a temperature of 35° C., a crude preparation of Subtilisin Carlsberg (10 mL, Alcalase 2.4L, Novo Laboratories) was added. Sodium hydroxide solution (6M) was used to maintain the reaction at pH 7.5–8.0. After 3 days, the acetone was removed under reduced pressure and the aqueous phase was extracted with CHCl$_3$ (1L) to remove the unreacted ester. The aqueous phase was adjusted to pH 7 with 3M HCl and was desalted by eluting through a column of Amberlite XAD-16(2 kg, prewashed sequentially with water, methanol, and water) using a water to water/methanol gradient. Evaporation of the solvent afforded 46 g (70%) of a white solid: mp 184.5° C.; TLC (25% ethyl acetate/25% water/25% acetic acid/25% n-butanol) R$_f$=0.43; anal. (C$_{15}$H$_{22}$N$_2$O$_4$S.0.25 H$_2$O)
Calcd: C, 54.44; H, 6.85; N, 8.47.
Found: C, 54.77; H, 6.53; N, 8.39.

EXAMPLE 3H

Diethyl (2-Bromoallyl)acetamidomalonate

To a stirred mixture of diethyl acetamidomalonate (217 g, 1.0 mol) and 2,3-dibromopropene (240 g, 1.2 mol) in dry tetrahydrofuran (2.50L), under nitrogen, was added sodium hydride (26.4 g, 1.1 mol) in several portions. The reaction mixture was stirred at room temperature for 30 min, then heated to reflux. After heating for 18 h, the resultant slurry was cooled to room temperature and suction filtered through a short pad of silica gel. The solid residue as washed with tetrahydrofuran (2×50 mL), and the filtrates were combined and concentrated. The residue was dissolved in ethyl acetate (2.0 L), washed with water and brine, and then was dried over MgSO$_4$. Filtration and concentration gave a yellow oil which solidified upon drying. The resultant solid was recrystallized from a mixture of hot ethyl acetate/hexane to give 301 g (89%) of the desired product: m.p. 85°–87° C.

EXAMPLE 3I

Diethyl (3-Bromo-2-oxo-propyl)acetamidomalonate

To a cold (0° C.), stirred solution of the resultant compound from Example 3H (280 g, 0.83 mol) in a mixture of 2:1 acetonitrile/water (1.68 L) was added solid N-bromosuccinimide (193 g, 1.08 mol) in three portions over a period of 15 min. The resultant orange mixture was stirred at 0° C. for an additional period of 1 h and then was allowed to warm to room temperature. After 4 h, the reaction mixture was treated with 10% aqueous sodium thiosulfate, diluted with ethyl acetate, and washed sequentially with water, 10% aqueous NaHSO$_4$ (3×) water, and brine. Drying (MgSO$_4$) and concentration afforded a yellow solid which was recrystallized from a mixture of ethyl acetate and hexane to give 247 g (85%) of the desired compound as a white solid: m.p. 97°–98.5° C.

EXAMPLE 3J

Diethyl (4-Thiazolylmethyl)acetamidomalonate

A 5 L, 3-neck round bottom flask equipped with a mechanical stirrer, stopper and a drying tube was charged with the resultant compound from Example 3I (325 g, 0.92 mol) and flushed with nitrogen. A freshly prepared solution of thioformamide in tetrahydrofuran (0.8M, 1.25 L) was added in one portion. The reaction mixture was stirred at room temperature for 4 h. The resultant slurry was then diluted with ether (1.25 L) and cooled to 0° C. The solid was then collected by suction filtration and washed with cold ether (3×) to give the title compound as the hydrochloride salt. This material was transferred to a 4 L separatory funel, slurried with ethyl acetate (2 L) and basified by the careful addition of 2M NaOH. The organic layer was separated, washed with water and brine, and then dried over MgSO$_4$. Filtration and concentration afforded a pale yellow oil which solidified upon drying to give 242 g of the desired compound. This material was recrystallized from an ethyl acetate/hexane mixture to afford 185.6 g (64%) of pure material: m.p. 104°–106° C.

EXAMPLE 3K

N-Acetyl-3-(4-thiazolyl)-DL-alanine Ethyl Ester

To a stirred solution of the resultant compound from Example 3J (185.6 g, 0.59 mol) in a mixture of tetrahydrofuran (620 mL) and ethanol (310 mL) was added aqueous 2M LiOH (325 mL, 0.65 mol) dropwise over 20 min. After stirring at room temperature for 2.5 h, the reaction mixture was concentrated and the resultant aqueous mixture was extracted with ether (3×200 mL), adjusted to pH 3 with 3M HCl, and concentrated under reduced pressure. Residual water was removed by evaporating portions of toluene (2×200 mL). The residue was diluted with toluene (1.5 L) and the resultant slurry was heated to reflux with separation of water (Dean-Stark trap). After 3 h the reaction mixture was cooled to room temperature, diluted with ethyl acetate (1.5 L) and suction filtered through SiO$_2$ (60 g). The solids were washed with additional ethyl acetate (4×500 mL) and the combined organics were concentrated to afford a pale yellow oil which solidified on drying (0.5 torr) to afford 119.6 g (84%) of the desired compound: m.p. 58°–62° C.

EXAMPLE 3L

N-Acetyl-3-(4-thiazolyl)-L-alanine and N-Acetyl-3-(4-thiazolyl)-D-alanine Ethyl Ester A 5 L, 3-neck round bottom flask equipped with a mechanical stirrer was charged with the resultant compound from Example 3K (210 g, 0.87 mol), distilled water (1.6 L), and 1M aqueous KCl (0.8 L). The homogeneous solution was adjusted to pH 7.0 with 0.1M NaOH and then was treated with Subtilisin Carlsberg (1.8 g) dissolved in 0.1M aqueous KCl (25 mL). The reaction mixture was stirred at room temperature with 1.0M NaOH added as required to maintain the pH at 6.25–7.25. After 4 h, 430 mL of base had been consumed and the reaction was judged to be complete. The reaction mixture was then extracted with chloroform (4×1.5 L), the aqueous phase was carefully acidified to pH 4 with 2M HCL and then was concentrated under reduced pressure. Residual water was removed by consecutive evaporation of portions of toluene (3×500 mL) and ethanol (3×500 mL). The residue was taken up in warm ethanol and suction filtered to remove inorganic salts. The solids were washed with warm ethanol (3×400 mL). The residue was taken up in warm ethanol and suction filtered to remove inorganic salts. The solids were washed with warm ethanol (3×400 mL) and the filtrates were concentrated to afford 92.6 g (50%) of N-acetyl-3-(4-thiazolyl)-L-alanine as a white solid: m.p. 186° C.

The combined chloroform fractions from the extractions were washed with saturated aqueous NaHCO$_3$, water, and brine and then were dried over MgSO$_4$. Filtration and concentration gave 103 g (49%) of N-acetyl-3-(4-thiazolyl)-D-alanine ethyl ester. This material could be further purified by recrystallization from ethyl acetate/hexane: m.p. 79°–80.5° C.

EXAMPLE 3M

Epimerization of N-Acetyl-3-(4-thiazolyl)-D-alanine Ethyl Ester

A 2 L round bottom flask equipped with a magnetic stirrer, reflux condenser, and nitrogen inlet was charged with sodium (0.96 g, 0.045 mol) and ethanol (900 mL) and the mixture was allowed to reflux until the sodium was consumed. The resultant solution of sodium ethoxide was cooled slightly, and N-acetyl-3-(4-thiazolyl)-D-alanine ethyl ester from Example 3L (102 g, 0.42 mol) was added. The reaction mixture was then heated to reflux. After 3 h the solution was cooled to room temperature, quenched with glacial acetic acid (0.045 mol) and concentrated to remove ethanol. The residue was diluted with ethyl acetate, washed with water and brine and dried over MgSO$_4$. Filtration and concentration gave a yellow oil which was purified by recrystallizing from a mixture of hot ethyl acetate and hexane to yield 89 g (87%) of material identical to that obtained from Example 3L.

EXAMPLE 3N 3-(4-Thiazolyl)-L-alanine Dihydrochloride

A 2 L round bottom flask equipped with a magnetic stirrer was charged with N-acetyl-3-(4-thialzoyl)-L-alanine from Example 3L (92.6 g, 0.43 mol) and 6M HCl (1 L). The resultant solution was heated to reflux. After 3 h the mixture was allowed to cool to room temperature. The solution was then concentrated under reduced pressure, evaporated from toluene (3×200 mL), and dried under vacuum overnight to give 120 g of a slightly wet solid. This material was used in the next reaction without further purification.

EXAMPLE 3O

N-Boc-3-(4-thiazolyl)-L-alanine

A 4 L Erlenmeyer flask equipped with a mechanical stirrer was charged with the resultant compound from Example 3N (125.9 g) and tetrahydrofuran (1.5 L) and the mixture was adjusted to pH 6.6 with saturated aqueous sodium bicarbonate. The resultant solution was then adjusted to pH 8.9 with 3.0M NaOH and a solution of di-tert-butyldicarbonate (117.8 g, 0.51 mol) in tetrahydrofuran (150 mL) as added. The reaction mixture was vigorously stirred at room temperature for 40 h. The tetrahydrofuran was removed under vacuum, the pH of the residue was adjusted to 2.0 with 3.0M HCl and the mixture was extracted with ethyl acetate (3×300 mL). The combined extracts were dried over MgSO$_4$, filtered, and concentrated to give 150 g of a white solid. Recrystallization from hot 1:1 ethyl acetate/hexane (1.06 L) gave 107.6 g (82% from the resultant compound of Example 3M) of the desired compound: m.p. 115° C.; [alpha]$_D$= +129.8 (c=1.04, CHCl$_3$).

Anal. (C$_{11}$H$_{16}$N$_2$O$_2$). Calcd: C, 48.53; H, 5.88; N, 10.29. Found: C, 48.58; H, 5.91; N, 10.17.

EXAMPLE 3P

Boc-L-(4-Thiazolyl)Ala Amide of (2S, 3R, 4S)-2-Amino-1-cyclohexyl-3,4-dihydroxy-6-methylheptane (2S,3R,4S)-2-[(tert-Butyloxycarbonyl)amino]-1-cyclohexyl-3,4-dihydroxy-6-methylheptane (5.05 g, 14.7 mmol, Luly et al., J. Org. Chem. 1988, 53, 6109) was stirred for 90 min in 4M HCl in ethanol and then evaporated. Ether was added and evaporated 3 times and the residue was dried under high vacuum. To this residue was added 1-hydroxybenzotriazole (5.57 g, 41.2 mmol), the resultant acid from Example 3O (4.00 g, 14.7 mmol), dimethylformamide (60 mL) and N-methylmorpholine (3.40 mL, 30.9 mmol). The mixture was cooled to −23° C., treated with 1-(3-dimethylaminopropyl)-3-ethylcarbodiimide hydrochloride (4.03 g, 21.0 mmol). After 2 h at −23° C. and 21 h at ambient temperature the mixture was poured into saturated NaHCO$_3$ solution and extracted into ethyl acetate. The organic layer was washed with water and brine, then, dried over Na$_2$SO$_4$ and evaporated to a white solid which was recrystallized from 1:15 (v/v) methylene chloride/ether (multiple crops) affording 6.28 g (86%) of the desired product as a flaky white solid: m.p. 159°-169° C; TLC (15% CH$_3$OH/85% CHCl$_3$) R$_f$=0.63; $^1$H NMR (CDCl$_3$) delta 8.75 (1H,d), 7.14 (1H, d), 6.18 (2H, br d), 4.44 (1H, dd), 4.27 (1H, m), 4.10 (1H, m), 3.37 (1H, dd), 3.30–3.12 (3H, m), 1.89 (1H, septet), 1.46 (9H, s), 0.94 (3H, d), 0.88 (3H, d).

Anal. (C$_{25}$H$_{43}$N$_3$O$_5$S). Calcd: C, 60.33; H, 8.71; N, 8.44. Found: C, 60.43; H, 8.68; N, 8.51.

EXAMPLE 3Q

H-L-(4-Thiazolyl)Ala Amide of (2S,3R,4S)-2-Amino-1-cyclohexyl-3,4-dihydroxy-6-methylheptane Trifluoroacetic acid (50 mL) was slowly added via cannula to a solution of the resultant compound from Example 3P (6.27 g, 12.6 mmol) in methylene chloride (50 mL) at 0° C. The reaction was stirred 3 h at 0° C. and concentrated in vacuo (40° C. bath) to an oil which was basified to pH 10-11 with aqueous K$_2$CO$_3$. The product was extracted into chloroform, dried over Na$_2$SO$_4$, filtered, and concentrated to a foam. Recrystallization from 1:4 (v/v) methylene chloride/hexane gave 5.00 g (100%) of the desired product as a fluffy white solid: m.p. 111°-112° C.; TLC (15% CH$_3$OH/85% CHCl$_3$) R$_f$=0.4; $^1$H NMR (CDCl$_3$) delta 8.77 (1H, d), 7.40 (1H, br d), 7.13 (1H, d), 4.54 (1H, m), 4.25 (1H, m), 3.80 (1H, dd), 3.33 (1H, dd), 3.25–3.12 (3H, m), 0.95 (3H, d), 0.86 (3H, d).

Anal (C$_{20}$H$_{35}$N$_3$O$_3$S) Calcd: C, 60.42; H, 8.87; N, 10.57. Found: C, 60.05; H, 8.65; N, 10.42.

EXAMPLE 3R (2S)-2-Benzyl-3-(1-methylpiperazin-4-ylsulfonyl)propionyl-(L)-(4-Thiazolyl)Ala Amide of (2S,3R,4S)-2-Amino-1-cyclohexyl-3,4-dihydroxy-6-methylheptane To the resultant acid from Example 3G (1.000 g, 3.064 mmol), the resultant amine from Example 3Q (1.110 g, 2.792 mmol), and 1-hydroxybenzotriazole (1.022 g, 7.563 mmol) in dimethylformamide (20 mL) was added N-methylmorpholine (0.35 mL, 3.2 mmol). The mixture was cooled to −23° C. and treated with 1-(3-dimethylaminopropyl)-3-ethylcarbodiimide hydrochloride (0.760 g, 3.96 mmol). After 2 h at −−23° C. and 14 h at ambient temperature, the reaction was poured into saturated NaHCO$_3$ solution (100 mL) and extracted into ethyl acetate (2×50 mL) which was washed with water (2×50 mL) and brine (50 mL) and then was dried over Na$_2$SO$_4$ and evaporated to afford 1.94 g. Recrystallization from ethanol (15 mL)/hexane (90 mL) afforded 1.559 g (79%) of a white solid: m.p. 169°-170° C.; TLC (10% CH$_3$OH/90% CHCl$_3$) R$_f$=0.40; $^1$H NMR (CDCl3) delta 8.73 (1H, d), 7.43 (1H, d), 7.37–7.16 (6H, m), 6.23 (1H, d), 4.63 (1H, dd), 2.30 (3), 0.95 (3H, d), 0.87 (3H, d).

Anal. (C$_{35}$H$_{55}$N$_5$O$_6$S20.75 H$_2$O) Calcd: C, 58.43; H, 7.91; N, 9.73. Found: C, 58.51; H, 7.74; N, 9.60.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfate, glucoheptonate, glycerophosphate, hemisulfate, heptonate, hexanoate, fumarate, hydrochloride, hydrobromide, hydroiodide, 2-hydroxy-ethanesulfate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

Examples of acids which may be employed to form pharmaceutically acceptable acid addition salts include such inorganic acids as hydrochloric acid, sulphuric acid, and phosphoric acid and such organic acids as oxalic acid, maleic acid, fumaric acid, succinic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters include a hydroxyl-substituted compound of the invention which has been acylated with a blocked or unblocked amino acid residue, a phosphate function, or a hemisccinate residue. The amino acid esters of particular interest are glycine and lysine; however, other amino acid residues can also be used. Other esters include the compounds of the invention wherein a carboxylic acid group has been esterified to provide esters which include, but are not limited to, methyl, ethyl or benzyl esters. These esters serve as prodrugs of the compounds of the present invention and serve to increase the solubility of these substances in the gastrointestinal tract. The prodrugs are metabolically converted in vivo to parent compound of the invention. The preparation of the pro-drug esters is carried out by reacting a hydroxyl-substituted compound of the invention with an activated amino acyl, phosphoryl or hemisuccinyl derivative. The resulting product is then deprotected to provide the desired pro-drug ester. Prodrugs which are esters of carboxylic acid group containing compounds of the invention are prepared by methods known in the art.

The novel method of this invention is directed to the use of a renin inhibitor in humans or other mammals for prevention, treatment, inhibition or reversal of renal dysfunction and renal diseases and in particular renal failure, including acute renal failure (which includes post surgical oliguria) and chronic renal failure.

This invention is also directed to renin inhibitor compositions useful for prevention, treatment, inhibition or reversal of renal dysfunction and renal diseases and in particular renal failure.

The effect of a renin inhibitor on renal failure can be demonstrated by observing the effects on renal hemodynamics that ultimately can alter GFR of a renin inhibitor administered to animals in which acute renal failure has been modeled, for example by ischemia, ureteral obstruction or nephrotoxic agents such as gentamicin, cis-platin and the like. In addition the effects of a renin inhibitor on chronic renal failure can be demonstrated by observing the effects on proteinuria, histopathologic improvement and long term stabilization of GFR of a renin inhibitor administered to animals in which chronic renal failure has been modeled, for example by reduced renal mass, puromycin-induced nephrosis or diabetic nephropathy.

Total daily dose administered to a host in single or divided doses may be in amounts, for example, from 0.001 to 10 mg/kg body weight daily and more usually 0.01 to 1 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, by nasal spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. Topical administration may also involve the use of ocular inserts. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, dextrose solution, mannitol solution, Ringer's solution, and isotonic chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Injectable preparations can be in ready to use form or reconstituted from a lyophilized powder.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Solid dosage forms can also comprise agents for enhancing oral absorption. Solid dosage forms can also comprise liquid filled capsules, for example PEG solutions of the active compound in a soft elastic gelatin capsule.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for treating or inhibiting renal dysfunction in a human comprising administering to said human a therapeutically effective amount of a compound of the formula:

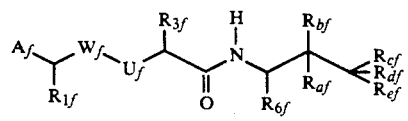

wherein $A_f$ is hydrogen, loweralkyl, arylalkyl, —OR$_{10f}$ or —SR$_{10f}$ wherein R$_{10f}$ is hydrogen, loweralkyl or aminoalkyl, —NR$_{11f}$R$_{12f}$ wherein R$_{11f}$ and R$_{12f}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkylamino)alkoxycarbonylalkyl, ((N-protected)alkylamino)alkoxycarbonylalkyl and (dialkylamino)alkoxycarbonylalkyl; or $A_f$ is

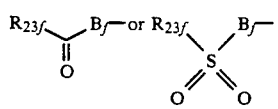

wherein $B_f$ is NH, alkylamino, S, O, CH$_2$ or CHOH and R$_{23f}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl(alkyl))amino, aminoalkyl, N-protectedaminoalkyl, alkylaminoalkyl, (N-protected)(alkyl)aminoalkyl, dialkylaminoalkyl, carboxyalkoxyalkyl, (alkoxycarbonyl)alkoxyalkyl, carboxyalkyl, carboxyalkylamino, alkoxycarbonylalkyl, alkoxycarbonylalkylamino, (amino)carboxyalkyl, (amino)carboxyalkylamino, ((N-protected)amino)carboxyalkyl, ((N-protected)amino)carboxyalkylamino, (alkylamino)carboxyalkyl, (alkylamino)carboxyalkylamino, ((N-protected)alkylamino)carboxyalkyl, ((N-protected alkylamino)carboxyalkylamino, (dialkylamino)carboxyalkyl, (dialkylamino)carboxyalkylamino, (amino)alkoxycarbonylalkyl, (amino)alkoxycarbonylalkylamino, ((N-protected)amino)alkoxycarbonylalkyl, ((N-protected)amino)alkoxycarbonylalkylamino, (alkylamino)alkoxycarbonylalkyl, (alkylamino)alkoxycarbonylalkylamino, ((N-protected)alkylamino)alkoxycarbonylalkyl, ((N-protected)alkylamino)alkoxycarbonylalkylamino, (dialkylamino)alkoxycarbonylalkyl, (dialkylamino)alkoxycarbonylalkylamino, aminocycloalkyl, aminoalkylamino, dialkylaminoalkyl(alkyl)amino, arylalkylamino, arylalkyl(alkyl)amino, alkoxyalkyl(alkyl)amino,(polyalkyoxy)alkyl(alkyl)amino, di-(alkoxyalkyl)amino, di-(hydroxyalkyl)amino, di-((polyalkoxy)alkyl)amino, polyalkoxy, (polyalkoxy)alkyl, (heterocyclic)alkyl or a substituted or unsubstituted heterocyclic wherein saturated heterocyclics may be unsubstituted, monosubstituted or disubstituted with hydroxy, oxo amino, alkylamino, dialkylamino, alkoxy, polyalkoxy or loweralkyl; unsaturated hetercyclics may be unsubstituted or monosubstituted with hydroxy, amino, alkylamino, dialkylamino, alkoxy, polyalkoxy or loweralkyl;

$W_f$ is C=O or CHOH;

$U_f$ is CH$_2$ or NR$_{2f}$ provided that when $W_f$ is CHOH then $U_f$ is CH$_2$; R$_{1f}$ is loweralkyl, cycloalkylmethyl, benzyl, 4-methoxybenzyl, halobenzyl, (1-naphthyl)methyl, (2-naphthyl)methyl, (4-imidazolyl)methyl, (alpha,alpha)dimethylbenzyl, 1-benzyloxyethyl, phenethyl, phenoxy, thiophenoxy, or anilino; provided that when R$_{1f}$ is phenoxy, thiophenoxy or anilino, then $B_f$ is CH$_2$ or CHOH or $A_f$ is hydrogen;

R$_{2f}$ is hydrogen or loweralkyl;

R$_{3f}$ is loweralkyl, loweralkenyl,((alkoxy)alkoxy)loweralkyl, (thioalkoxy)alkyl, benzyl or heterocyclic ring substituted methyl;

R$_{6f}$ is loweralkyl, cycloalkylmethyl or benzyl;

R$_{af}$ is vinyl, formyl, hydroxymethyl or hydrogen;

R$_{df}$ is hydrogen or loweralkyl;

R$_{bf}$ and Ref are independently selected from OH and NH$_2$; and

R$_{cf}$ is hydrogen, loweralkyl, vinyl or arylalkyl; or a pharmaceutically acceptable salt, ester or prodrug thereof.

2. The method of claim 1 wherein the renal dysfunction is chronic renal failure or acute renal failure.

3. A method for treating or inhibiting renal dysfunction in a human comprising administering to said human a therapeutically effective amount of H-((beta,-betadimethyl)-beta-Ala)-(4-OCH$_3$)Phe-His amide of 2(S)-amino-1-cyclohexyl-3(R),4(S)-dihydroxy-6-methylheptane or a pharmaceutically acceptable salt, ester or prodrug thereof.

4. A method for treating or inhibiting renal dysfunction in a human comprising administering to said human a therapeutically effective amount of 2(S)-2-Benzyl-3-(1-methylpiperazin-4-ylsulfonyl)-propionyl-(L)-(4-thiazolyl)Ala amide of (2S,3R,4S)-2-amino-1-cyclohexyl-3,4-dihydroxy-6-methylheptane or a pharmaceutically acceptable salt, ester or prodrug thereof.

* * * * *